(12) United States Patent
Song et al.

(10) Patent No.: US 11,790,512 B2
(45) Date of Patent: Oct. 17, 2023

(54) DEFECT INSPECTION DEVICE

(71) Applicant: SuaLab Co., Ltd., Seoul (KR)

(72) Inventors: Kiyoung Song, Seoul (KR); Hunmin Cho, Seoul (KR)

(73) Assignee: SuaLab Co., Ltd., Seoul (KR)

( * ) Notice: Subject to any disclaimer, the term of this patent is extended or adjusted under 35 U.S.C. 154(b) by 145 days.

(21) Appl. No.: 17/425,666

(22) PCT Filed: Jan. 3, 2020

(86) PCT No.: PCT/KR2020/000110
§ 371 (c)(1),
(2) Date: Jul. 23, 2021

(87) PCT Pub. No.: WO2020/153623
PCT Pub. Date: Jul. 30, 2020

(65) Prior Publication Data
US 2022/0092765 A1    Mar. 24, 2022

(30) Foreign Application Priority Data

Jan. 24, 2019 (KR) ........................ 10-2019-0009273

(51) Int. Cl.
*G06T 7/00* (2017.01)
*G06V 10/40* (2022.01)
(Continued)

(52) U.S. Cl.
CPC ....... *G06T 7/0004* (2013.01); *G01N 21/8806* (2013.01); *G01N 21/8901* (2013.01);
(Continued)

(58) Field of Classification Search
CPC ......... G06T 7/0004; G06T 2207/10152; G06T 2207/20084; G01N 2033/0078; G01N 21/8806; G01N 21/8901; G01N 21/9515; G01N 2021/9518; G01N 2021/887; G01N 2021/8883; G01N 21/89; G01N 2201/061;
(Continued)

(56) References Cited

U.S. PATENT DOCUMENTS 11,488,294 B2 * 11/2022 Wen ................. G02F 1/1309
2012/0249779 A1   10/2012 Ji et al.
(Continued)

FOREIGN PATENT DOCUMENTS

JP    2000-005705 A    1/2000
JP    2005-241469 A    9/2005
(Continued)

OTHER PUBLICATIONS

Japan Patent Office, Office Action from Japanese Patent Application No. 2021-543228, dated Aug. 2, 2022 (8 pages).

*Primary Examiner* — Boubacar Abdou Tchoussou
(74) *Attorney, Agent, or Firm* — Brian B. Shaw, Esq.; Harter Secrest & Emery LLP

(57) ABSTRACT

The defect inspection device includes a robot arm including a hold unit for holding an object and a driving unit for moving the object; a first camera unit photographing an exterior of the object; an illumination unit irradiating light to
(Continued)

the exterior of the object; and a control unit determining whether there is a defect in the object based on an image of the object photographed by the first camera unit.

16 Claims, 12 Drawing Sheets

(51) Int. Cl.
  *G01N 21/88*   (2006.01)
  *G01N 21/89*   (2006.01)
  *H04N 7/18*   (2006.01)
  *H04N 23/56*   (2023.01)
  *H04N 23/80*   (2023.01)
  *H04N 23/90*   (2023.01)
  *G01N 33/00*   (2006.01)

(52) U.S. Cl.
  CPC .............. *G06V 10/40* (2022.01); *H04N 7/181* (2013.01); *H04N 23/56* (2023.01); *H04N 23/80* (2023.01); *H04N 23/90* (2023.01); *G01N 2033/0078* (2013.01); *G06T 2207/10152* (2013.01)

(58) Field of Classification Search
  CPC ........ G06V 10/40; H04N 7/181; H04N 23/56; H04N 23/80; H04N 23/90; H04N 23/61; H04N 23/74; B23Q 3/155; B23Q 3/157; B23Q 5/22; B23Q 3/1552; B23Q 3/15713; B23Q 2003/155407
  See application file for complete search history.

(56) References Cited

U.S. PATENT DOCUMENTS

| | | | |
|---|---|---|---|
| 2015/0130925 A1 | 5/2015 | Park et al. | |
| 2016/0267647 A1* | 9/2016 | Higo | G06T 7/0004 |
| 2018/0186004 A1 | 7/2018 | Park et al. | |
| 2020/0005422 A1* | 1/2020 | Subramanian | G06T 7/194 |
| 2020/0388021 A1 | 12/2020 | Song et al. | |
| 2021/0056681 A1* | 2/2021 | Hyatt | G05B 19/41875 |
| 2021/0150695 A1* | 5/2021 | Yogo | G01B 11/25 |
| 2022/0005183 A1* | 1/2022 | Hyatt | H04N 23/90 |

FOREIGN PATENT DOCUMENTS

| | | |
|---|---|---|
| JP | 2015-135253 A | 7/2015 |
| JP | 2017-026441 A | 2/2017 |
| JP | 2018-059830 A | 4/2018 |
| JP | 2019-007891 A | 1/2019 |
| KR | 10-0753614 B1 | 8/2007 |
| KR | 10-2012-0046494 A | 5/2012 |
| KR | 10-1175595 B1 | 8/2012 |
| KR | 10-2012-0109915 A | 10/2012 |
| KR | 10-2014-0090808 A | 7/2014 |
| KR | 10-1520636 B1 | 5/2015 |
| KR | 10-1707206 B1 | 2/2017 |
| KR | 10-1736458 B1 | 5/2017 |
| KR | 10-2018-0080630 A | 7/2018 |
| KR | 10-1916347 B1 | 11/2018 |

* cited by examiner

DEFECT INSPECTION DEVICE

TECHNICAL FIELD

The present disclosure relates to factory automation equipment, and more particularly, to a device for inspecting a defect of an object.

BACKGROUND ART

In the process of producing an object at a factory, the object may be defective due to machinery, process, or other reasons. In the factory, it is common to go through a procedure to check whether the object is defective before production of the object is completed and the object is released.

However, when a person checks whether there is a defect in the completed object, time and cost consumption is large and in the case of a defect that is hard to visually check, there may be a problem in that an object which is not normally produced is released. Accordingly, there is a demand for a device that can efficiently determine whether the object is defective in the art.

Korean Patent Registration No. 10-1707206 discloses a gripper transfer device.

DISCLOSURE

Technical Problem

The present disclosure has been made in an effort to provide a defect inspection device.

TECHNICAL SOLUTION

Technical Solution

In order to implement the above-described object, according to an embodiment of the present disclosure, a defect inspection device includes: a robot arm including a hold unit for holding an object and a driving unit for moving the object; a first camera unit photographing an exterior of the object; an illumination unit irradiating light to the exterior of the object; and a control unit determining whether there is a defect in the object based on an image of the object photographed by the first camera unit.

In an alternative embodiment, the defect inspection device may further include a display unit displaying at least one image of the image of the object photographed by the first camera unit and an image in which whether there is the defect in the object is displayed.

In an alternative embodiment, the defect inspection device may further include: a transport unit transporting the object for defect inspection; and a classification transport unit classifying and transporting the object based on a result of the defect inspection of the control unit for the object.

In an alternative embodiment, the driving unit may include at least one driving shaft for rotating the object.

In an alternative embodiment, the driving unit may adjust an arrangement state of the object so that the first camera unit photographs the object in a different arrangement state to acquire images photographed at different timings.

In an alternative embodiment, the defect inspection device may further include a second camera unit for photographing the object before being held by the hold unit, in which the control unit allows the hold unit to be aligned to hold the object based on the arrangement state of the object based on the image of the object acquired by the second camera unit.

In an alternative embodiment, the illumination unit of the defect inspect device may include two or more sub illumination units irradiating light, and the illumination unit may have a space formed therein, the first camera unit may be located on one side of the space and may photograph an object arranged on the other side of the space by the robot arm through the space, and the control unit may allow the robot arm to arrange the object on the other side of the space so that the first camera photographs the object.

In an alternative embodiment, in the sub illumination unit, a light emitting unit configured in a in a corn or polypyramid shape and irradiating the light to an internal surface of a horn shape may be located.

In an alternative embodiment, the two or more sub illumination units may be configured in the corn or polypyramid shape, and ratios of widths of lower surfaces and widths of upper surfaces of the horn shape of respective sub illumination units may be different from each other.

In an alternative embodiment, the illumination unit of the defect inspection device may irradiate two or more different types of light to the exterior of the object.

In an alternative embodiment, the control unit of the defect inspection device may determine whether there is the object based on two or more images photographed under different illumination conditions, respectively.

In an alternative embodiment, the control unit of the defect inspection device may determine whether there is the defect in the object based on two or more images acquired by photographing an object in a first arrangement state under different illumination conditions and two or more images acquired by photographing an object in a second arrangement state under different illumination conditions.

In an alternative embodiment, the control unit of the defect inspection device may set the two or more images as inputs of two or more channels included in a defect inspection model including one or more network functions, respectively to extract features of the two or more input images, respectively by using the defect inspection model, and determine whether there is anomaly for each of the two or more images based on the extracted features.

In an alternative embodiment, when it is determined that there is the anomaly in at least one image of the two or more images, the control unit of the defect inspection device may determine that there is the defect in the object.

In an alternative embodiment, the control unit of the defect inspection device may calculate a first normal image photographed under a first illumination condition and a second normal image photographed under a second illumination condition which are normal images which are a basis of anomaly determination by using both images as inputs of channels included in a first sub model included in the defect inspection model, respectively, calculate a first determination object image photographed under the first illumination condition and a second determination object image photographed under the second illumination condition which are anomaly determination object images by using both images as inputs of channels included in a second sub model included in the defect inspection model, respectively, and determine whether there is the defect in the object based on a calculation result of the first sub model and the second sub model.

In an alternative embodiment, the defect inspection model of the defect inspection device may further include a comparator connected to at least one of the first sub model and the second sub model in series.

In an alternative embodiment, in the defect inspection device, a first channel of the first sub model into which the first normal image is input may share at least one link having the same weight as a first channel of the second sub model into which the first determination object image is input, and a second channel of the first sub model into which the second normal image is input may share at least one link having the same weight as a second channel of the second sub model into which the second determination object image is input.

In an alternative embodiment, the control unit of the defect inspection device may generate comparison information of at least one first layer based on at least one layer of the first channel of the first sub model and at least one layer of the first channel of the second sub model, and transfers the first layer comparison information to a corresponding layer of the first channel of the comparator to calculate anomaly information of the first determination object image, and generate comparison information of at least one second layer based on at least one layer of the second channel of the first sub model and at least one layer of the second channel of the second sub model, and transfers the second layer comparison information to a corresponding layer of the second channel of the comparator to calculate the anomaly information of the second determination object image.

Advantageous Effects

According to an embodiment of the present disclosure, a defect inspection device can be provided.

BEST MODE

Figure 1:
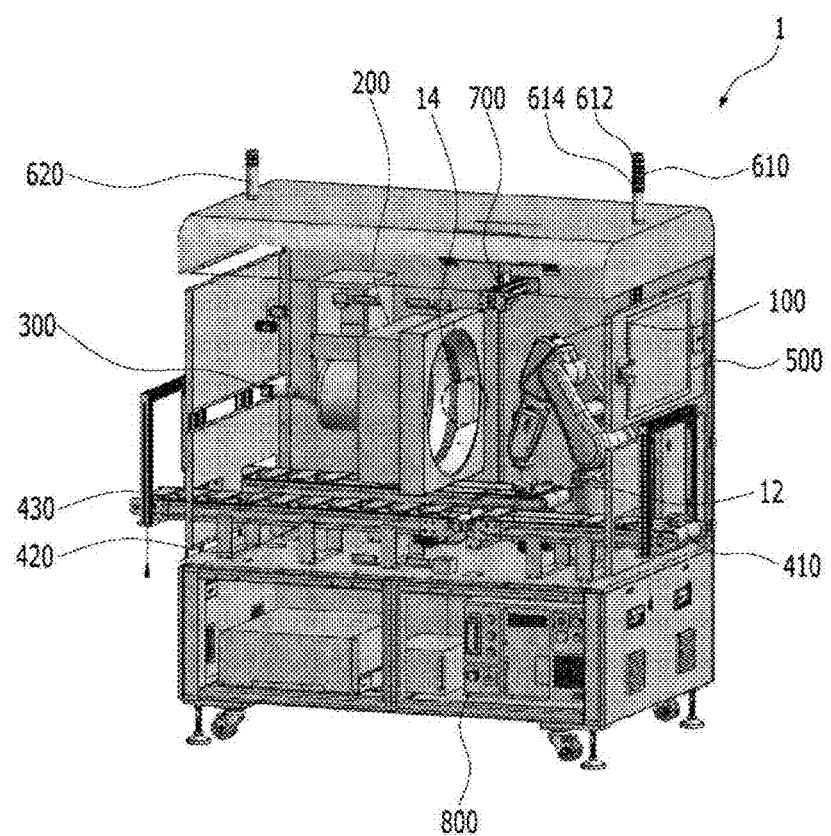
FIG. 1 is a diagram schematically illustrating a defect inspection device according to an embodiment of the present disclosure.

Various embodiments will now be described with reference to drawings and like reference numerals are used to refer to like elements throughout all drawings. In the present specification, various descriptions are presented to provide appreciation of the present disclosure. However, it is apparent that the embodiments can be executed without the specific description.

"Component", "module", "system", and the like which are terms used in the specification refer to a computer-related entity, hardware, firmware, software, and a combination of the software and the hardware, or execution of the software. For example, the component may be a processing process executed on a processor, the processor, an object, an execution thread, a program, and/or a computer, but is not limited thereto. For example, both an application executed in a computing device and the computing device may be the components. One or more components may reside in the processor and/or the execution thread and one component may be localized in one computer or distributed among two or more computers. Further, the components may be executed by various computer-readable media having various data structures, which are stored therein. The components may perform communication through local and/or remote processing according to a signal (for example, data from one component that interacts with other components and/or data from other systems through a network such as the Internet through a signal in a local system and a distribution system) having one or more data packets, for example.

Moreover, the term "or" is intended to mean not exclusive "or" but inclusive "or". That is, when not separately specified or not clear in terms of a context, a sentence "X uses A or B" is intended to mean one of the natural inclusive substitutions. That is, the sentence "X uses A or B" may be applied to any of the case where X uses A, the case where X uses B, or the case where X uses both A and B. Further, it should be understood that the term "and/or" used in this specification designates and includes all available combinations of one or more items among enumerated related items.

Further, it should be appreciated that the term "comprise" and/or "comprising" means presence of corresponding features and/or components. However, it should be appreciated that the term "comprises" and/or "comprising" means that presence or addition of one or more other features, components, and/or a group thereof is not excluded. Further, when not separately specified or it is not clear in terms of the context that a singular form is indicated, it should be construed that the singular form generally means "one or more" in this specification and the claims.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

FIG. 1 is a diagram schematically illustrating a defect inspection device according to an embodiment of the present disclosure.

Referring to FIG. 1, a defect inspection device 1 may include a robot arm 100, an illumination unit 200, a first camera unit 300, a transport unit 410, classification transport units 420 and 430, a display unit 500, light output units 610 and 620, a second camera unit 700, and a control unit 800. The defect inspection device 1 may include subordinate elements including a housing, a cover, a support block, a bracket, etc., for supporting the above-described components. However, the above-described components are not required for implementing the defect inspection device 1 and the defect inspection device 1 may thus have components more or less than components listed above.

The defect inspection device 1 may be a device for inspecting whether there is a defect in an object 10. The defect inspection device 1 is implemented by components to be described below to inspect the defect of the object 10. The object 10 may be an object of determination of whether there is the defect. The object 10 is not the component of the defect inspection device 1, but is an auxiliary component for describing a configuration or an operation of the defect inspection device 1. For example, the defect inspection device 1 may determine whether there is the defect in a part which is a part of a product or determine whether there is the defect in a finished product. A detailed description of a role of the above-described defect inspection device is just an example and the present disclosure is not limited thereto.

Figure 2:
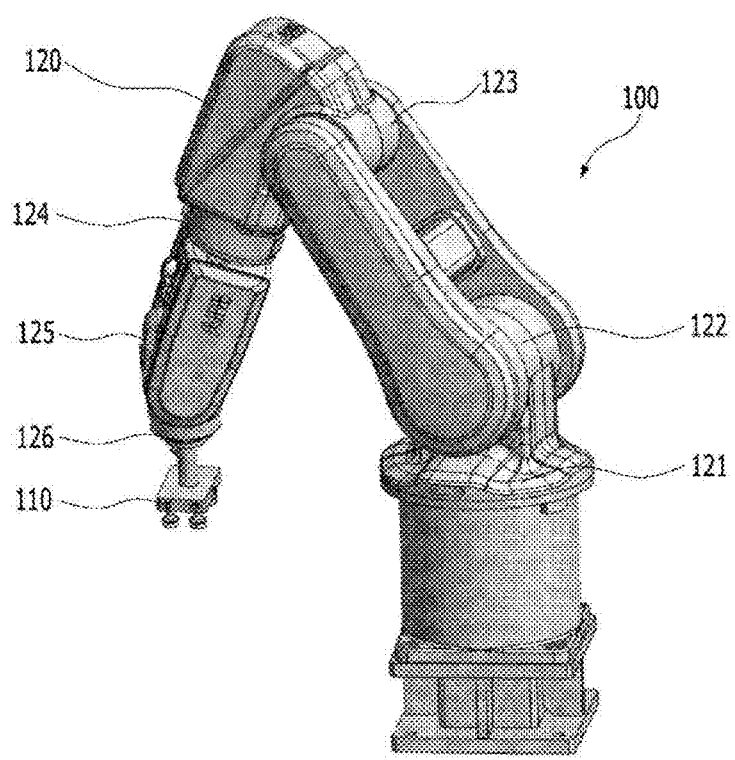
FIG. 2 is a diagram illustrating a robot arm applied to a defect inspection device according to an embodiment of the present disclosure.

The robot arm 100 may hold and move the object 10. The robot arm 100 will be described with reference to FIG. 2.

The robot arm 100 may include a hold unit 110 for holding the object 10 and a driving unit 120 for driving the object 10.

The robot arm 100 may hold and move the object 10 transported from the outside to the inside of the defect inspection device 1 through the transport unit 410 for defect inspection. The robot arm 100 may hold the object located at a first position 12 above the transport unit 410. The robot arm 100 may move the object 10 located at the first position 12 to be located at a second position 14. The robot arm 100 may move the object 10 to be located at the second position 14 so that the object 10 may be photographed through the first camera unit 300 for defect inspection. The first position 12 may be a position for one side of the transport unit 410. The first position 12 may be a position at which the object 10 transported from the outside to the inside of the defect inspection device 1 through the transport unit 410 is stopped and disposed in order to hold the object 10 by the robot arm 100. The second position 14 may be a position which allows at least a part of the object 10 to be included in an image acquired by photographing of the first camera unit 300. The robot arm 100 may move an object of which defect inspection is completed to the classification transport units 420 and 430 from the second position 14 in order to transport the object from the inside to the outside of the defect inspection device 1. The robot arm 100 may move the object 10 to a first classification transport unit 420 or a second classification transport unit 430 based on whether there is the defective in the object 10.

The driving unit 120 of the robot arm 100 may move the object 10. According to an embodiment of the present disclosure, the driving unit 120 of the robot arm 100 may move the object 10 from the first position 12 to the second position 14. According to an embodiment of the present disclosure, the driving unit 120 of the robot arm 100 may adjust the object 10 to be differently disposed at the second position 14. The driving unit 120 may adjust an arrangement state of the object 10 so that the first camera unit 300 may acquire images photographed at different timings by photographing the object 10 in the different arrangement state. For example, the driving unit 120 may move the object 10 to a first arrangement state so that the first camera unit 300 may acquire an image in which an upper portion of the object 10 is photographed, and move the object 10 from the first arrangement state to the second arrangement state 10 so as to acquire an image in which a lateral portion of the object 10 is photographed again. For example, when a size of the object 10 is larger than a range photographable by a wide angle of the first camera unit 300, the driving unit 120 may move the object 10 for dividing photographing. For example, the driving unit 120 may move the object 10 so as to photograph a first part of one surface of the object, and then, photograph a remaining second part other than the first part of the same surface for the dividing photographing. For example, when the object 10 is a hexahedron, the driving unit 120 may change the arrangement state of the object 10 at the second position 14 5 times in order to photograph each of six surfaces by the first camera unit 300. A detailed description of the operation of the driving unit 120 described above is just an example and the present disclosure is not limited thereto.

The driving unit 120 of the robot arm 100 may have a multi-shaft articulated structure. The driving unit 120 of the robot arm 100 may include at least one driving shaft 121, 122, 123, 124, 125, or 126 for rotating the object 10 in order to move the object 10. For example, the robot arm 100 may be a structure in which the robot arm 100 operates with 6 joints with 6 rotational shafts. The driving unit 120 of the robot arm 100 may include a first driving shaft 121, a second driving shaft 122, a third driving shaft 123, a fourth driving shaft 124, a fifth driving shaft 125, and a sixth driving shaft 126. One or more driving shafts included in the driving unit 120 may be spaced apart from each other. The sixth driving shaft 126 may be connected to the hold unit 110 of the robot arm 100. A detailed description of the robot arm 100 described above is just an example and the present disclosure is not limited thereto, and the robot arm 100 may have various structures to move the object 10.

Figure 3:
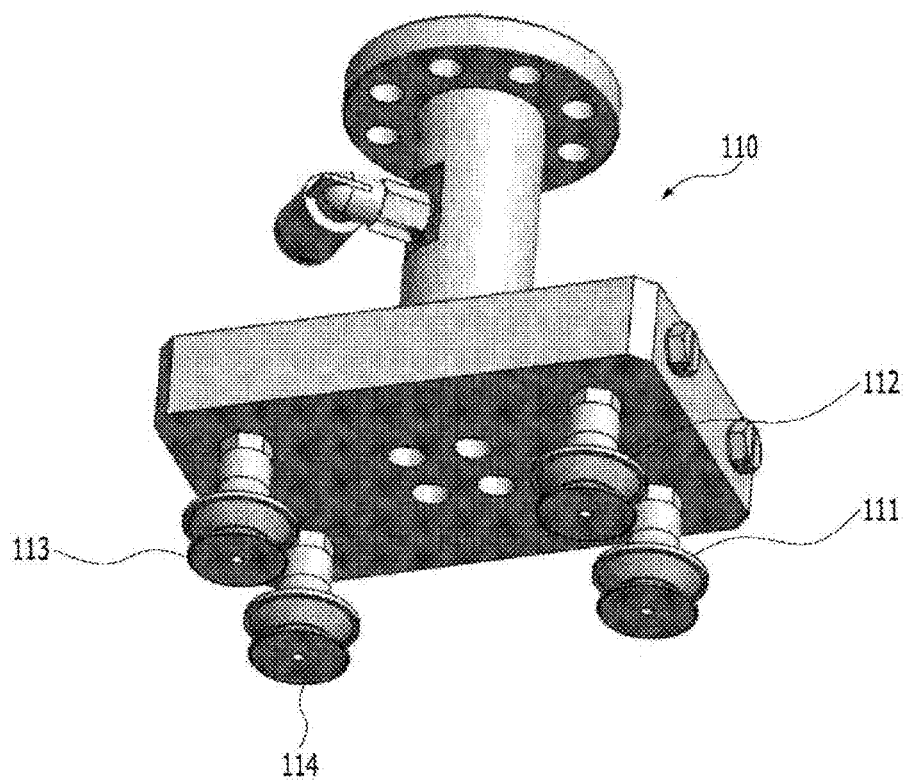
FIG. 3 is a diagram illustrating a hold portion which is a part of the robot arm applied to the defect inspection device according to an embodiment of the present disclosure.

The hold unit 110 of the robot arm 100 will be described with reference to FIG. 3. The hold unit 110 of the robot arm 100 may hold the object 10. The hold unit 110 of the robot arm 100 may hold the object 10 located at the first position 12 on the transport unit 410 in order to detect whether there is the defect in the object 10. The hold unit 110 of the robot arm 100 may separate the object 10 from the robot arm 100 so that the object 10 may be located on the classification transport units 420 and 430 after detecting whether there is the defect in the object 10 is completed. The hold unit 110 of the robot arm 100 may prevent the object 10 from being dropped in the process of detecting whether there is the defect by holding the object 10. The description of the operation of the robot arm 100 for the object is just an example and the present disclosure is not limited thereto.

The hold unit 110 of the robot arm 100 may be constituted by one or more sub hold units 111, 112, 113, and 114. One or more sub hold units 111, 112, 113, and 114 may be arranged to be spaced apart from each other. The hold unit 110 may include sub hold units of different numbers according to a shape of an object 10 to be held. One or more sub hold units 111, 112, 113, and 114 may be arranged differently according to the shape of the object 10 to be held. For example, the hold unit 110 of the robot arm 100 may be constituted by a first sub hold unit 111, a second sub hold unit 112, a third sub hold unit 113, and a fourth sub hold unit 114. For example, when one surface of the object 10 has a square shape, the first sub hold unit 111, the second sub hold unit 112, the third sub hold unit 113, and the fourth sub hold unit 114 may be arranged in the square shape. For example, when one surface of the object 10 is a surface which is not flat and is stepped, two or more respective sub hold units may be constituted by sub hold units having different lengths. The detailed description of the arrangement and the number of sub hold units included in the hold unit 110 described above is just an example and the present disclosure is not limited thereto.

According to an embodiment of the present disclosure, the sub hold units 111, 112, 113, and 114 of the robot arm 100 may hold the object 10 by using a pressure. For example, the sub hold units 111, 112, 113, and 114 may hold the object 10 by using a hydraulic pressure or an air pressure. The sub hold units 111, 112, 113, and 114 may be compressed by inhaling external air through an inlet located on the bottom of the sub hold units 111, 112, 113, and 114. The external air inhaled through the inlet of the sub hold units 111, 112, 113, and 114 may be discharged through an outlet. The object 10 may be compressed to the bottom of the sub hold units 111, 112, 113, and 114 by a pressure difference caused while the external air passes through the sub hold units 111, 112, 113, and 114. The detailed description of the sub hold units 111, 112, 113, and 114 described above is just an example and the present disclosure is not limited thereto, and the hold unit 110 may have various structures for holding the object 10.

According to an embodiment of the present disclosure, the sub hold units 111, 112, 113, and 114 of the robot arm 100 may hold the object 10 by using an electromagnetic force. The sub hold units 111, 112, 113, and 114 may receive power to generate the electromagnetic force, and closely attach or adsorb one surface of the object 10 onto the sub hold units 111, 112, 113, and 114 by the electromagnetic force. The sub hold units 111, 112, 113, and 114 additionally inject the air onto one surface of the object 10 through a bottom injection nozzle of the sub hold units 111, 112, 113, and 114 to form a clearance from the object 10. The sub hold units 111, 112, 113, and 114 may also allow the object 10 to move with a predetermined interval from the sub hold units 111, 112, 113, and 114 by using electromagnetic force and air injection. The detailed description of the sub hold units 111, 112, 113, and 114 described above is just an example and the present disclosure is not limited thereto, and the hold unit 110 may have various structures for holding the object 10.

According to an embodiment of the present disclosure, the sub hold units 111, 112, 113, and 114 of the robot arm 100 are configured by a suction pad or a vacuum pad to hold the object 10. The sub hold units 111, 112, 113, and 114 may be configured to be elastically closely attached to the object 10. The detailed description of the sub hold units 111, 112, 113, and 114 described above is just an example and the present disclosure is not limited thereto, and the hold unit 110 may have various structures for holding the object 10.

According to an embodiment of the present disclosure, the sub hold units 111, 112, 113, and 114 of the robot arm 100 are configured by a clipper to hold the object 10. For example, the clipper may be configured by a needle pin. The sub hold units 111, 112, 113, and 114 may fix and lift up both ends of the object 10 by using the clipper. The detailed description of the sub hold units 111, 112, 113, and 114 described above is just an example and the present disclosure is not limited thereto, and the hold unit 110 may have various structures for holding the object 10.

Figure 4:
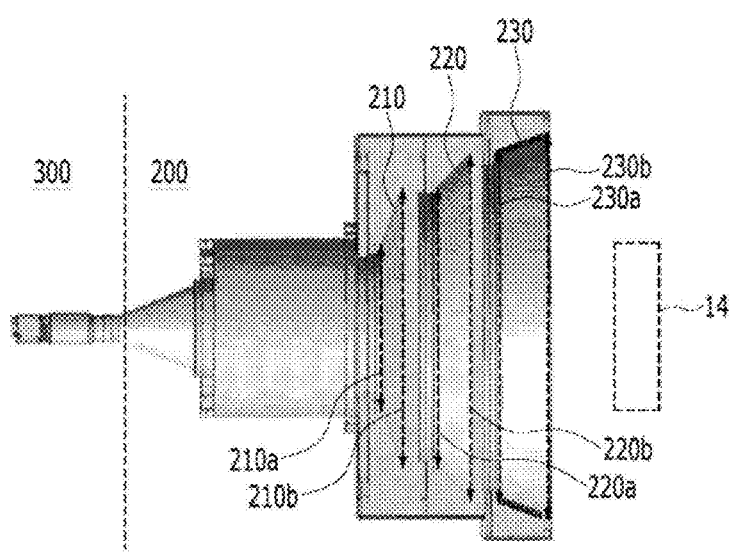
FIG. 4 is a cross-sectional view of an illumination unit applied to the defect inspection device according to an embodiment of the present disclosure.
Figure 5:
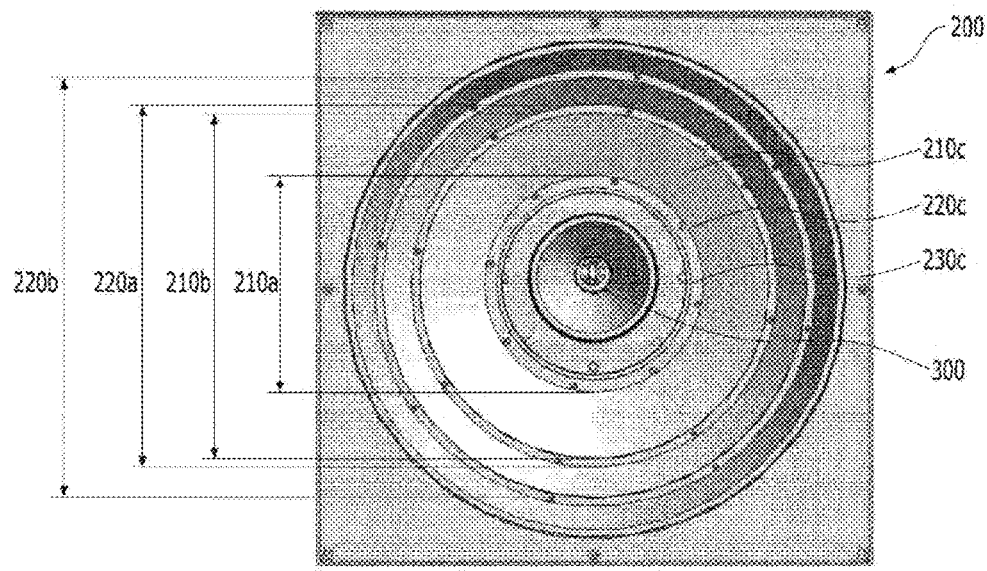
FIG. 5 is a front view of the illumination unit applied to the defect inspection device according to an embodiment of the present disclosure.

The illumination unit 200 will be described with reference to FIGS. 4 and 5. FIG. 4 is a cross-sectional view of an illumination unit applied to the defect inspection device according to an embodiment of the present disclosure. FIG. 5 is a front view of the illumination unit applied to the defect inspection device according to an embodiment of the present disclosure.

The illumination unit 200 may be a component of the defect inspection device 1 for irradiating light to an exterior of the object 10. The illumination unit 200 may irradiate the light to the exterior of the object 10 when the object 10 is located at the second position 14 in order to inspect the defect. Each of light emitting units 210c, 220c, and 230c located on internal surfaces of two or more sub illumination units 210, 220, and 230 constituting the illumination unit 200, respectively may be arranged to irradiate the light to the object 10 at the second position 14. The illumination unit 200 may irradiate two or more different types of light to the exterior of the object 10. The illumination unit 200 may irradiate, to the exterior of the object 10, at least one light of intensities of two or more different light, a color of light, a direction of light, and a pattern of light. For example, a first illumination unit 210 included in the illumination unit 200 may irradiate light at a first angle based on one surface of the object 10 and a second illumination unit 220 may irradiate light at a second angle based on one surface of the object 10.

The illumination unit 200 may be constituted by two or more sub illumination units 210, 220, and 230. The illumination unit 200 may have a space formed therein. The illumination unit 200 may be constituted by two or more sub illumination units 210, 220, and 230 having spaces formed therein. The sub illumination units 210, 220, and 230 may be configured in a horn shape. The sub illumination units 210, 220, and 230 may be configured in a corn or polypyramid shape. Thicknesses of the sub illumination units 210, 220, and 230 may be constant, and the sub illumination units 210, 220, and 230 may be configured in a shape to surround a horn. A space may be formed at the center of the horn of the sub illumination units 210, 220, and 230. The first camera unit 300 may be located on one side of an internal space of the illumination unit 200 and the object 10 may be located on the other side by the robot arm 100, and as a result, the first camera unit 300 may photograph the exterior of the object 10 through the internal space. The sub illumination units 210, 220, and 230 may include light emitting units 210c, 220c, and 230c that irradiate light to at least a part of an internal surface of the horn shape. For example, the light emitting units 210c, 220c, and 230c may be an LED illumination, a near infrared light illumination, a near ultraviolet light illumination, etc., but the present disclosure is not limited thereto.

The illumination unit 200 may be constituted by two steps or more sub illumination units. In the illumination unit 200, a first sub illumination unit 210, a second sub illumination unit 220, and a third sub illumination unit 230 may be connected in series around the internal space. Two or more sub illumination units 210, 220, and 230 constituting the illumination unit 200 may be arranged to be spaced apart from each other. A detailed description of the arrangement state of the sub illumination units 210, 220, and 230 is just an example and the present disclosure is not limited thereto, but the sub illumination units 210, 220, and 230 may be arranged by another method for irradiating the light to the object 10.

The illumination unit 200 may be constituted by two or more sub illumination units 210, 220, and 230 having different shapes. Two or more sub illumination units 210, 220, and 230 may be different from each other in ratio of width of a lower surface and a width of an upper surface of the horn shape. The above-described lower and upper surfaces are just terms for describing the shapes of the sub illumination units 210, 220, and 230, and the surfaces are not actually formed, and portions corresponding to the lower and upper surfaces of the horn are portions which are opened in the sub illumination units 210, 220, and 230 and form the internal space of the illumination unit 200. A ratio of a width 210a of the upper surface of the first sub illumination unit and a width 210b of the lower surface of the first sub illumination unit may be different from a ratio of a width 220a of the upper surface of the second sub illumination unit and a width 220b of the lower surface of the second sub illumination unit. The ratio of the width 210a of the upper surface of the first sub illumination unit and the width 210b of the lower surface of the first sub illumination unit may be different from a ratio of a width 230a of the upper surface of the third sub illumination unit and a width 230b of the lower surface of the third sub illumination unit. That is, referring to a cross-sectional view on a lateral surface of the illumination unit 200, an angle of the first sub illumination unit, an angle of the second sub illumination unit, and an angle of the third sub illumination unit may be different. A detailed description of the shapes of the sub illumination units 210, 220, and 230 is just an example and the present disclosure is not limited thereto, but the sub illumination units 210, 220, and 230 may be formed by another method for irradiating the light to the object 10.

Two or more sub illumination units 210, 22, and 230 constituting the illumination unit 200 may emit light based on a predetermined order. According to an embodiment of the present disclosure, each of two or more sub illumination units 210, 220, and 230 constituting the illumination unit 200 may be emitted at different timings. For example, the first sub illumination unit 210 is turned on and photographing of the object 10 is completed, and then the first sub illumination unit 210 may be turned off, and the second sub illumination unit 220 may be turned on. According to an embodiment of the present disclosure, each of two or more sub illumination units 210, 220, and 230 constituting the illumination unit 200 may be turned on at the same time or at different timings. For example, the first sub illumination unit 210 and the second sub illumination unit 220 may be turned on at a first timing and the third sub illumination unit may be turned on at a second timing. A detailed description of an emitting order or a turn-on timing of the illumination unit 200 described above is just an example, and the present disclosure is not limited thereto.

When the defect of the object 10 is inspected based on irradiating two or more different types of light to the exterior of the object 10, the same effect as holding and visually inspecting the object 10 under the light by a person may be obtained. Defect inspection is performed by using two or more different types of light to detect even all defects of the object 10 which may be checked only under the light having a specific direction, a specific type, a specific intensity, etc. Even a defective portion which is shown differently according to the direction of the light may be detected by irradiating different types of light to increase the accuracy of the defect inspection device 1.

The first camera unit 300 may be a component of the defect inspection device 1 for photographing the exterior of the object 10. The first camera unit 300 will be described with reference to FIGS. 4 and 5. The first camera unit 300 may be connected to the illumination unit 200. The first camera unit 300 is disposed on one side of the illumination unit 200 to photograph the exterior of the object 10 disposed on the other side of the illumination unit 200. When the object 10 is disposed at the second position 14 which is the other side of the illumination unit 200, the first camera unit 300 may photograph the object 10.

According to an embodiment of the present disclosure, when the object 10 is disposed by the robot arm 100, the first camera unit 300 may photograph two or more images under different illumination conditions. For example, in respect to the exterior of the object 10 in the same arrangement state, the first camera unit 300 photographs the object 10 to acquire a first determination object image when irradiating the light of the first sub illumination unit 210 to the exterior of the object 10, photographs the object 10 to acquire a second determination object image, and photographs the object 10 to acquire a third image when irradiating the light of the third sub illumination unit 210 to the exterior of the object 10. The detailed description of the photographing method of the first camera unit 300 described above is just an example and the present disclosure is not limited thereto.

According to an embodiment of the present disclosure, whenever the object 10 is rearranged by the robot arm 100 and stopped, the first camera unit 300 may photograph the exterior of the object 10. The robot arm 100 may change the arrangement state of the object 10 at the second position 14 so that the first camera unit 300 may photograph the other surface of the object 10 at the other angle. For example, the first camera unit 300 may photograph a left lateral surface of the object 10 in a first arrangement state of the object 10, and then photograph a right lateral surface of the object 10 when the object 10 is changed from the first arrangement state to a second arrangement state by the robot arm 100. The detailed description of the photographing method of the first camera unit 300 described above is just an example and the present disclosure is not limited thereto.

The first camera unit 300 may capture various types of images. A photographing result of the first camera unit 300 may include a 3D image, a black and white image, a GIF image stored with time, a video image, an infrared image, an electronic image, and the like. Further, the first camera unit 300 may include a film camera, a digital camera, a microscope, a magnifier, an infrared camera, an ultraviolet (UV) camera, an X-Ray, a magnetic resonance imaging (MRI) device, and a predetermined image acquiring device. The configuration of the first camera unit 300 may vary depending on a photographed thing of a photographed object 10.

According to an embodiment of the present disclosure, the first camera unit 300 photographs the object 10 in the first arrangement state under two or more illumination conditions to acquire two or more images and photographs the object 10 in the second arrangement state under two or more illumination conditions to acquire two or more other images.

The defect inspection device 1 may determine whether there is the defect in the object 10 based on the image which the first camera unit 300 acquires by photographing the object 10.

Figure 6:
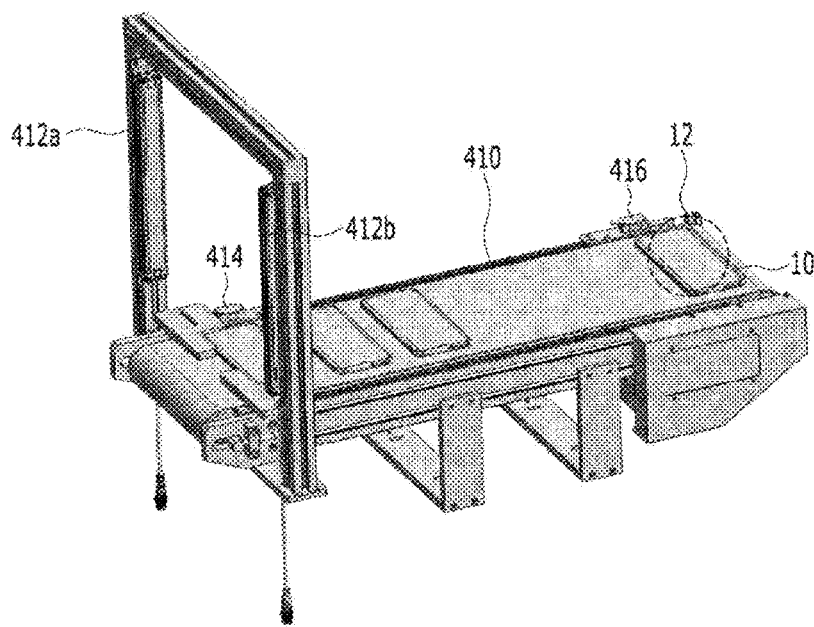
FIG. 6 is a diagram illustrating a transport unit applied to the defect inspection device according to an embodiment of the present disclosure.

The transport unit 410 may transport the object 10 for the defect inspection. The transport unit 410 will be described with reference to FIG. 6.

The transport unit 410 may transport the object 10 from the outside of the defect inspection device 1 to the inside of the defect inspection device 1. For example, the transport unit 410 may be configured by a conveyor belt, but this is just an example, but the present disclosure is not limited thereto.

The transport unit 410 may include a transport unit first sensor 414 installed outside the defect inspection device 1 and a transport unit second sensor 416 installed inside the defect inspection device 1. The transport unit first sensor 414 may sense that the object 10 is placed on one side of the transport unit 410. When the object 10 is sensed by the transport unit first sensor 414, the transport unit 410 operates to transport the object 10 to the inside of the defect inspection device 1. The transport unit second sensor 416 may sense that the object 10 is transported from one side to the other side of the transport unit 410. When the object 10 is sensed by the transport unit second sensor 416, the transport unit 410 may stop to operate to locate the object 10 at the first position 12. When the object 10 is sensed by the transport unit second sensor 416, the robot arm 100 may hold and move the object 10 at the first position 12. A detailed description of one or more sensors included in the transport unit 410 described above is just an example, but the present disclosure is not limited thereto.

The transport unit 410 may include transport unit third sensors 412*a* and 412*b* installed outside the defect inspection device 1. When an object is sensed between a left transport unit third sensor 412*a* and a right transport unit third sensor 412*b*, the operation of the transport unit 410 may be stopped. For example, the transport unit third sensors 412*a* and 412*b* may be infrared sensors. For example, when the transport unit third sensors 412*a* and 412*b* sense a part (e.g., a hand) of a human body of a person, the operation of the transport unit 410 may be stopped. All components of the transport unit third sensors 412*a* and 412*b* described above are not required and another component may be further added or the above-described components may be excluded. A detailed description of the transport unit third sensors 412*a* and 412*b* is just an example and the present disclosure is not limited thereto.

Figure 7:
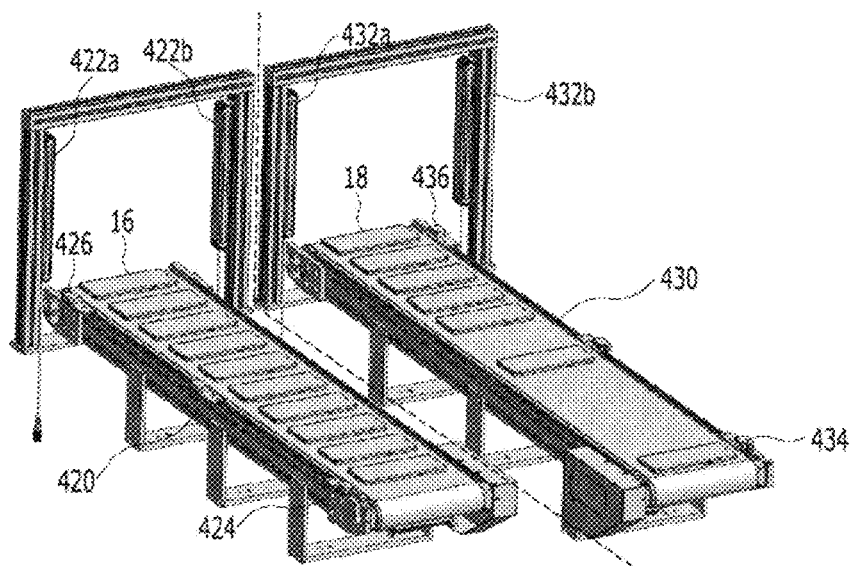
FIG. 7 is a diagram illustrating a classification transport unit applied to the defect inspection device according to an embodiment of the present disclosure.

The classification transport units 420 and 430 may classify and transport the object based on a defect inspection result for the object 10. The classification transport units 420 and 430 will be described with reference to FIG. 7.

The classification transport units 420 and 430 may include a first classification transport unit 420 and a second classification transport unit 430. When there is no defect in an object 16, the first classification transport unit 420 may transport the object 16 from the inside to the outside of the defect inspection device 1. When there is no defect in an object 18, the second classification transport unit 430 may transport the object 18 from the inside to the outside of the defect inspection device 2. The classification transport units 420 and 430 may be configured by the conveyor belt, but this is just an example, but the present disclosure is not limited thereto. When there is no defect in the object 16 based on the defect inspection result for the object 10, the robot arm 100 may move and put down the object 16 to be placed on the first classification transport unit 420 and when there is the defect in the object 18, the robot arm 100 may move and put down the object 18 to be placed on the second classification transport unit 430.

The classification transport units 420 and 430 may include classification transport unit first sensors 424 and 434 installed inside the defect inspection device 1 and classification transport unit second sensors 426 and 436 installed outside the defect inspection device 1. The classification transport unit first sensors 424 and 434 may sense that the object 10 for which whether the defect inspection is performed is completed is placed on one side of each of the classification transport units 420 and 430. When the object 10 is sensed by the classification transport unit first sensors 424 and 434, the classification transport units 420 and 430 operate to transport the object 10 to the outside of the defect inspection device 1. The classification transport unit second sensors 426 and 436 may sense that the object 10 is transported from one side to the other side of the classification transport units 420 and 430. When the object 10 is sensed by the classification transport unit second sensors 426 and 436, it is recognized that the object 10 moves to the outside of the defect inspection device 1, and as a result, the operations of the classification transport units 420 and 430 may be stopped. A detailed description of one or more sensors included in the classification transport units 420 and 430 described above is just an example, but the present disclosure is not limited thereto.

The classification transport units 420 and 430 may include classification transport unit third sensors 422*a*, 422*b*, 432*a*, and 432*b* installed outside the defect inspection device 1. When the object is sensed between left classification transport unit third sensors 422*a* and 432*a* and right classification transport unit third sensors 422*b* and 432*b*, the operations of the transport units 420 and 430 may be stopped. For example, the classification transport unit third sensors 422*a*, 422*b*, 432*a*, and 432*b* may be infrared sensors. For example, when the classification transport unit third sensors 422*a*, 422*b*, 432*a*, and 432*b* sense a part (e.g., a hand) of the human body of the person, the operations of the classification transport units 420 and 430 may be stopped. All components of the classification transport unit third sensors 422*a*, 422*b*, 432*a*, and 432*b* described above are not required and another component may be further added or the above-described components may be excluded. A detailed description of the classification transport unit third sensors 422*a*, 422*b*, 432*a*, and 432*b* is just an example, but the present disclosure is not limited thereto.

The display unit 500 may display at least one image of an image of the object 10 photographed by the first camera unit 300 and an image in which whether there is the defect in the object 10 is displayed. The display unit 500 may be attached onto an outer surface of the defect inspection device 1. The image in which whether there is the defect in the object 10 is displayed may be an image indicating whether there is the defect or an image displaying at which position of the object 10 there is the defect. For example, when there is anomaly data in the image acquired by photographing the object 10 in the second arrangement state and it is determined that there is the defect in the object 10, the display unit 500 may display a position of the object 10 in the second arrangement state and having the defect. A detailed description of a display operation of the display unit 500 described above is just an example, but the present disclosure is not limited thereto. The display unit 500 may be configured as predetermined visual output devices including an LCD, an LED, a CRT, and the like. The examples and components of the display are just examples and the present disclosure is not limited thereto.

A first light output unit 610 may display whether there is the defect in the object 10. A first sub light output unit 612 may be emitted when there is the defect in the object 10 and a second sub light output unit 614 may be emitted when there is no defect in the object 10. For example, when there is no defect in the object 10, a green light emitting unit may be emitted and when there is the defect, a red light emitting unit may be emitted. When objects 10 of a predetermined number or more is loaded on at least one of the transport unit 410, and the classification transport units 420 and 430, a second light output unit 620 may display a notification. The detailed description of the light output unit described above is just an example and the present disclosure is not limited thereto.

The second camera unit 700 may photograph the object 10 before the object 10 is held by the hold unit 110. When the defect inspection device 1 is vertically looked down from the top, the second camera unit 700 may be attached to a vertical upper position of the first position 12 of the defect inspection device 1. When the transport unit 410 stops to place the object 10 at the first position 12, the second camera unit 700 may photograph the object 10. The hold unit 110 of the robot arm 100 may be aligned to hold the object 10 based on the arrangement state of the object 10 based on the image of the object 10 acquired by the second camera unit 700. When the object 10 is placed parallel to the transport unit 410 at the first position on the transport unit 410, the hold unit 110 may also be aligned in parallel to hold the object 10. For example, the hold unit 110 may be aligned so that the first sub hold unit 111 is compressed to a first corner among four corners of one lateral surface of the object 10, the second sub hold unit 112 is compressed to a second corner among four corners of one lateral surface of the object 10, the third sub hold unit 113 is compressed to a third corner among four corners of one lateral surface of the object 10, and the fourth sub hold unit 114 is compressed to a fourth corner among four corners of one lateral surface of the object 10. The detailed description of the position of the second camera unit 700 and the alignment of the hold unit 110 is just an example, and the present disclosure is not limited thereto and may be implemented by all methods in which the second camera unit 700 photographs the object 10 and the hold unit 110 is aligned based on the arrangement state of the object 10 to hold the object 10.

The control unit 800 may control the operation of the defect inspection device 1. The control unit 800 may control at least one of the robot arm 100, the illumination unit 200, the first camera unit 300, the transport unit 410, the classification transport units 420 and 430, the display unit 500, the light output units 610 and 620, and the second camera unit 700 to operate.

Hereinafter, a defect inspection method for implementing the defect inspection device according to an embodiment of the present disclosure will be described.

In an embodiment of the present disclosure, a server may include other components for performing a server environment of the server. The server may include all arbitrary types of devices. The server as a digital device may be a digital device with a calculation capability, which has a processor installed therein and a memory, such as a laptop computer, a notebook computer, a desktop computer, a web pad, or a mobile phone. The server may be a web server that processes a service. A type of server described above is just an example and the present disclosure is not limited thereto.

Throughout the present specification, a model, a neural network, a network function, and a neural network may be used as the same meaning. The neural network may be generally constituted by an aggregate of calculation units which are mutually connected to each other, which may be called "node". The "nodes" may also be called "neurons". The neural network is configured to include one or more nodes. The nodes (alternatively, neurons) constituting the neural networks may be connected to each other by one or more "links".

In the neural network, one or more nodes connected through the link may relatively form the relationship between an input node and an output node. Concepts of the input node and the output node are relative and a predetermined node which has the output node relationship with respect to one node may have the input node relationship in the relationship with another node and vice versa. As described above, the relationship of the output node to the input node may be generated based on the link. One or more output nodes may be connected to one input node through the link and vice versa.

In the relationship of the input node and the output node connected through one link, a value of the output node may be determined based on data input in the input node. Here, a node connecting the input node and the output node to each other may have a weight. The weight may be variable and the weight is variable by a user or an algorithm in order for the neural network to perform a desired function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form the input node and output node relationships in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be configured to include one or more nodes. Some of the nodes constituting the neural network may constitute one layer based on distances from an initial input node. For example, an aggregation of nodes of which the distance from the initial input node is n may constitute an n layer. The distance from the initial input node may be defined by the minimum number of links which should be passed through for reaching the corresponding node from the initial input node. However, definition of the layer is predetermined for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which do not have other input nodes connected through the links. Similarly thereto, the final output node may mean one or more nodes which do not have the output node in the relationship with other nodes among the nodes in the neural network. Further, a hidden node may mean nodes constituting the neural network other than the initial input node and the final output node. In the neural network according to an embodiment of the present disclosure, the number of nodes of the input layer may be larger than the number of nodes of the hidden layer close to the output layer, and the neural network may be a neural network of a type in which the number of nodes decreases as the layer progresses from the input layer to the hidden layer.

A deep neural network (DNN) may refer to a neural network that includes a plurality of hidden layers in addition to the input and output layers. When the deep neural network is used, the latent structures of data may be determined. In other words, latent structures (e.g., what objects are in the picture, what the content and feelings of the text are, what the content and feelings of the voice are) of photos, text, video, voice, and music may be determined. The deep neural network may include a convolutional neural network (CNN), a recurrent neural network (RNN), a restricted Boltzmann machine (RBM), a deep belief network (DBN), a Q network, a U network, a Siamese network, and the like.

The convolutional neural network (CNN) as a type of deep neural network includes a neural network that includes a convolutional layer. The convolutional neural network is a type of multilayer perceptrons designed to use minimal preprocessing. The CNN may be constituted by one or more convolutional layers and artificial neural network layers associated therewith and may additionally use the weight and pooling layers. Such a structure allows the CNN to fully utilize the input data of a two-dimensional structure. The convolutional neural network may be used for recognizing an object in an image. The convolutional neural network may represent and process image data as a matrix having the dimension. For example, in the case of image data encoded in red-green-blue (RGB), the image data may be represented as a two-dimensional (for example, a two-dimensional image) matrix for each of R, G, and B colors. That is, a color value of each pixel of the image data may become a component of the matrix and a size of the matrix may be equal to the size of the image. Accordingly, the image data may be represented by three two-dimensional matrix (three-dimensional data array).

In the convolutional neural network, matrix components at respective positions of a convolutional filter and the image are multiplied by each other while moving the convolutional filter to perform a convolutional process (input/output of a convolutional layer). The convolutional filter may be constituted by an n*n type matrix and may be generally configured as fixed type filters of a number smaller than the number of all pixels of the image. In other words, when m*m images are input to the convolutional layer (e.g., a convolutional layer in which the size of the convolutional filter is n*n), a matrix representing n*n pixels including each pixel of the image may be a component multiplication with the convolutional filter (i.e., a multiplication of respective components of the matrix). Components matched with the convolutional filter may be extracted from the image by the multiplication with the convolutional filter. For example, a 3*3 convolutional filter for extracting a vertical straight line component from the image may be configured as [[0,1,0], [0,1,0],[0,1,0]] and when the convolutional filter is applied to an input image, the vertical straight line component matched with the convolutional filter may be extracted and output from the image. The convolutional layer may apply the convolutional filter to respective matrixes (i.e., R, G, and B colors in the case of R, G, and B coding images) for respective channels representing the image. The convolutional layer may extract features matched with the convolutional filter from the input image by applying the convolutional filter to the input image. A filter value (i.e., a value of each component of the matrix) of the convolutional filter may be updated by back propagation during a training process of the convolutional neural network.

A subsampling layer is connected to the output of the convolutional layer to simplify the output of the convolutional layer, thereby reducing a memory usage and a computational amount. For example, when the output of the convolutional layer is input to a pooling layer having a 2*2 max pooling filter, a maximum value included in each patch is output every 2*2 patches in each pixel of the image to compress the image. The aforementioned pooling may be a method that outputs a minimum value in the patch or outputs an average value of the patch and a predetermined pooling method may be included in the present disclosure.

The convolutional neural network may include one or more convolutional layers and subsampling layers. The convolutional neural network repeatedly performs the convolutional process and a subsampling process (e.g., the aforementioned max pooling) to extract the features from the image. The neural network may extract global features of the image through the repeated convolutional process and subsampling process.

The output of the convolutional layer or the subsampling layer may be input to a fully connected layer. The fully connected layer is a layer in which all neurons in one layer and all neurons in an adjacent layer are connected. The fully connected layer may mean a structure in which all nodes of each layer are connected to all nodes of another layer in the neural network.

In an embodiment of the present disclosure, the neural network may include a deconvolutional neural network (DCNN) in order to perform segmentation of the image data. The deconvolutional neural network may perform a similar operation to calculating the convolutional neural network in a reverse direction and output the feature extracted from the convolutional neural network as a picture map related to original data.

In the present specification, the network function may include one or more neural networks and in this case, an output of the network function may be an ensemble of outputs of one or more neural networks. A model may perform processing of data together with another model. The model may be interconnected to another model in series or in parallel. Hereinafter, the model may be written as a synonym with the neural network. A defect inspection model 900 may be referred to as a neural network 900, a first sub model 910 may be referred to as a first sub network 910, and a second sub model 930 may also be referred to as a second sub network 930.

Figure 8:
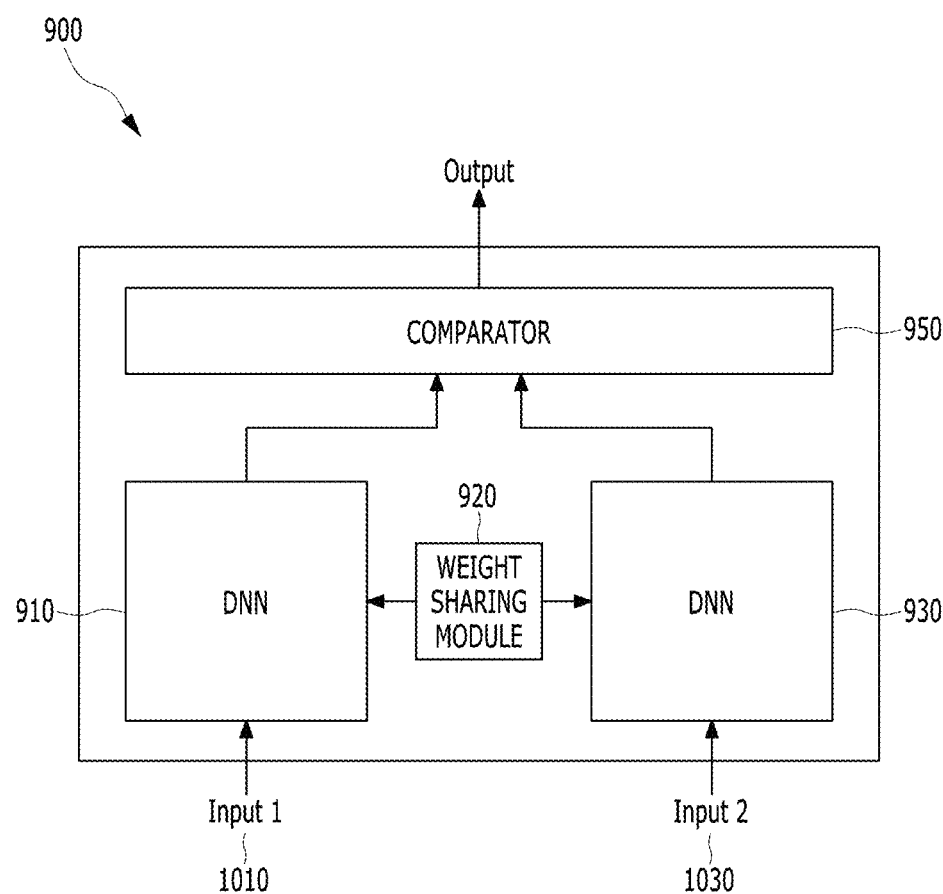
FIG. 8 is a diagram illustrating a Siamese network according to an embodiment of the present disclosure.

FIG. 8 is a diagram illustrating a Siamese network according to an embodiment of the present disclosure.

A Siamese network 900 is a neural network which may be used for a recognizer in which training data for each category is not sufficient. The Siamese network may learn similarity measurement from data. The Siamese network may include two or more neural networks 910 and 930 (sub networks) at least partially sharing a weight and a comparator 950 receiving outputs from the neural networks as illustrated in FIG. 8. At least two images may be input into the Siamese network 900. The Siamese network 900 may output a result of determining a similarity of two input images. For image processing, the Siamese network may include two convolutional neural networks receiving images. Two convolutional neural networks receiving the images in the Siamese network may share at least a part of the weight. The sub networks included in the Siamese network may share the weight by a weight sharing module 920, and the sub networks share the weight, and as a result, the Siamese network may extract and compare features for two input data with a common weight.

A Siamese network structure as a network structure capable of learning to measure the similarity of the input data may be used when there are many categories and data for training is not sufficient. A learning method of input data similarity measurement may include a process of finding a function to map an input pattern to a target space so that a simple distance in the target space is close to a semantic distance in an input space.

The learning method of the input data similarity measurement of the Siamese network 900 may include a process of calculating a weight w in a function $G_w(X)$ having the weight w of the sub network. Specifically, the learning method may include a process of calculating the weight w when input data $X_1$ and $X_2$ are in the same category in the function $G_w(X)$ of the sub network, a similarity function $E_w(X_1,X_2)=\|G_w(X_1)-G_w(X_2)\|$ has a small value and when the input data $X_1$ and $X_2$ are in different categories, the similarity function $E_w(X_1,X_2)=\|G_w(X_1)-G_w(X_2)\|$ has a large value. The weight w of the sub network may be shared by each weight sharing module 920. In the Siamese network structure, the sub network may process each input data with the function $G_w(X)$ having the shared weight.

Nodes of two convolutional neural networks, which correspond to each other may share the weight. The comparator 950 may compare a similarity between features output from the convolutional neural networks with each other. In this case, the comparison may be performed based on a mathematical distance of the features output from both convolutional neural networks. By a scheme of comparing both images, the Siamese network 900 may recognize an object, etc. in image data even when the training data is not sufficient and since the Siamese network 900 is not sensitive to rotation, transformation, etc., of the image data, the Siamese network 900 may have a general recognition capability.

The neural network may be learned in at least one scheme of supervised learning, unsupervised learning, and semi supervised learning. Learning of the neural network is to minimize errors in output. The learning of the neural network is a process of repeatedly inputting learning data into the neural network and calculating the output of the neural network for the learning data and the error of a target and back-propagating the errors of the neural network from the output layer of the neural network toward the input layer in a direction to reduce the errors to update the weight of each node of the neural network. In the case of the supervised learning, the learning data labeled with a correct answer is used for each learning data (i.e., the labeled learning data) and in the case of the unsupervised learning, the correct answer may not be labeled in each learning data. That is, for example, the learning data in the case of the supervised learning related to the data classification may be data in which category is labeled in each learning data. The labeled learning data is input to the neural network, and the error may be calculated by comparing the output (category) of the neural network with the label of the learning data. The calculated error is back-propagated in a reverse direction (i.e., a direction from the output layer toward the input layer) in the neural network and connection weights of respective nodes of each layer of the neural network may be updated according to the back propagation. A variation amount of the updated connection weight of each node may be determined according to a learning rate. Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the learning data may be generally a subset of actual data (i.e., data to be processed using the learned neural network) of actual data, and as a result, there may be a learning cycle in which errors for the learning data decrease, but the errors for the actual data increase. Overfitting is a phenomenon in which the errors for the actual data increase due to excessive learning of the learning data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the learning data, regularization, dropout of omitting a part of the node of the network in the process of learning, etc., may be applied.

Figure 9:
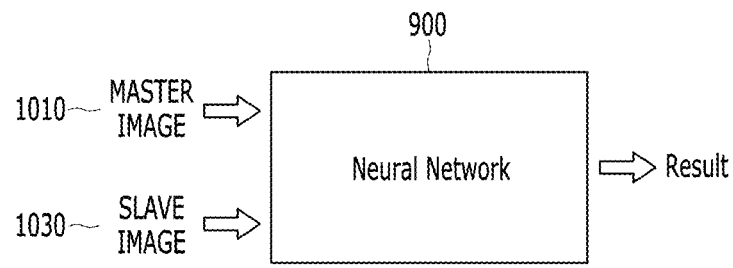
FIG. 9 is a conceptual diagram schematically illustrating a defect inspection method for implementing the defect inspection device according to an embodiment of the present disclosure.

FIG. 9 is a conceptual diagram schematically illustrating a defect inspection method for implementing the defect inspection device according to an embodiment of the present disclosure.

The defect inspection method of the present disclosure may be performed by one or more control units 800 of the defect inspection device 1. One or more control units 800 of the defect inspection device 1 of the present disclosure may perform a calculation process of the defect inspection model 900 of the present disclosure. All calculation processes (i.e., neural network learning, feature extraction, feature comparison, etc.) of the defect inspection method of the present disclosure may be performed by the control unit 800 of the defect inspection device 1. That is, an expression that the defect inspection model 900 processes data may mean a process in which the control unit 800 of the defect inspection device 1 executes the defect inspection model 900 to process the data.

In the defect inspection method of the present disclosure, the defect inspection device 1 may input a master image 1010 and a slave image 1030 into the defect inspection model 900, and output a result based on a similarity calculation result of both images, which is calculated in the defect inspection model 900.

The neural network of the present disclosure may be used for classification of data. For example, the neural network of the present disclosure may be used for anomaly detection.

Anomaly data may mean abnormal data which deviates from a normal pattern of data. The data may have an anomaly pattern, and the anomaly data may mean data which deviates from the anomaly pattern. For example, data regarding an image of a product in a production process may have an anomaly pattern that the product is a normal product and the anomaly data may be data (i.e., e.g., an image of a bad product, etc) which deviates from the anomaly pattern that the product is the normal product. The description of the normal data, the anomaly pattern, and the anomaly data of the present disclosure is just an example, and the present disclosure is not limited thereto.

More specifically, the neural network of the present disclosure may be used for classifying the anomaly product and the normal product in the production process. The anomaly product may be the object 18 having the defect and the normal product may be the object 16 having no defect. For example, the defect inspection model of the present disclosure may be used for inspecting whether there is the defect in the object 10. Further, the neural network of the present disclosure may be used for image segmentation. The image segmentation may mean a process of separating a part of the image to be distinguished from the other part. The image segmentation may include, for example, a process of separating a part of the image to be distinguished from the other part based on an edge, a color, etc., extracted from the image. Further, the image segmentation may be a process of extracting positional information of the anomaly part from the image to identify a position of the anomaly data from the other part of the image. Further, the image segmentation may also include a process of visualizing and displaying a part of the image distinguished from the other part. For example, the neural network of the present disclosure may be used for displaying the anomaly part in the image.

The master image 1010 is an image which is a basis of determining anomaly of input data. The slave image 1030 is an image which becomes an anomaly determination object. In the present disclosure, the master image 1010 may be used for referring to the same image as the normal image 1010 and the slave image 1030 may be used for referring to the same image as the determination object image 1030.

In the present disclosure, the anomaly data may be abnormal data which deviates from the normal pattern of data. For example, the anomaly data may be an image acquired by photographing the object 18 having the defect by the first camera unit 300. The master image 1010 may be an image including only normal-state image data not including the anomaly data. The slave image 1030 may be the normal pattern or the abnormal data, and may be an image which becomes an object for which the neural network determines whether the slave image 1030 is the normal pattern or the abnormal data. For example, the master image 1010 may be an image acquired by photographing the exterior of the object 16 having no defect, and the slave image 1030 may be an image acquired by photographing the exterior of the object 10 to be inspected.

The images input into the defect inspection model 900 may have the same size. Further, the image input into the defect inspection model 900 may be separated into a patch having a predetermined size in order to facilitate processing of the neural network and increase accuracy of classification by patch overlapping. For example, each of the master image 1010 and the slave image 1030 may be an image having a 256*256 pixel size, and each of them may be separated into a patch having a 32*32 pixel size to be input into the neural network, i.e., a sub model of the defect inspection model 900. Extraction the patch from the image may be performed for each pixel of the image, and each patch may have a portion overlapping each other. For example, when a patch of 32*32 pixels is extracted from a leftmost upper pixel of the image, and a patch of 32*32 pixels is extracted from a pixel adjacent to a right of the corresponding pixel, each patch may have an overlapping portion.

The defect inspection device 1 may extract the feature from each of the master image 1010 and the slave image 1030 input into the neural network 900. The defect inspection device 1 may determine the similarity between the master image 1010 and the slave image 1030 by comparing respective features. The defect inspection device 1 may determine the similarity by acquiring a mathematical distance between the feature of the master image 1010 and the feature of the slave image 1030. For example, when the similarity between the master image 1010 and the slave image 1030 is equal to or less than a predetermined threshold, the control unit 800 may determine the slave image 1030 as an image including the anomaly data. Further, the control unit 800 compares the feature of the master image 1010 and the feature of the slave image 1030 by the deep neural network to generate a pixel by pixel segmentation output of expressing which pixel is actually different in both images for each pixel. The defect inspection device 1 may compare the outputs of the sub networks by an arbitrary comparison algorithm. The defect inspection device 1 may just compare a difference between both features, and output a degree of a difference between both features, a position of a pixel of a portion having the difference, etc., by using the neural network for the comparison between both features.

Figure 10:
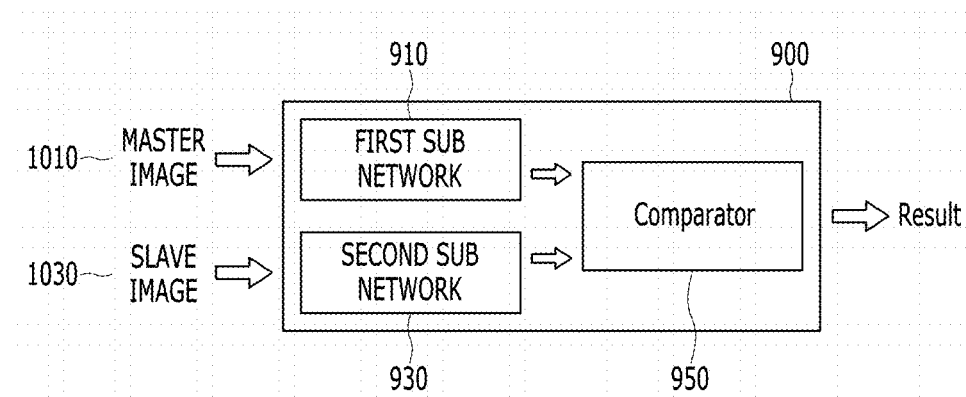
FIG. 10 is an exemplary diagram illustrating a configuration of a defect inspection model for implementing the defect inspection method according to an embodiment of the present disclosure.

FIG. 10 is an exemplary diagram illustrating a configuration of a defect inspection model for implementing the defect inspection method according to an embodiment of the present disclosure.

FIG. 10 is an exemplary diagram more specifically illustrating the schematic view of FIG. 9.

The master image 1010 and the slave image 1030 may be input into sub networks 910 and 930 of the neural network 900, respectively. The defect inspection device 1 calculate images input by using the respective sub networks 910 and 930, respectively to extract features of the input images, respectively. The sub networks 910 and 930 may constitute at least a part of the Siamese network. The sub networks 910 and 930 share at least a part of a weight with each other to allow a comparator 950 to extract the features with a common weight for each of the master image 1010 and the slave image 1030 and compare the extracted features. Here, the sub networks 910 and 930 may include the deep neural network structure. For example, at least one of the networks 910 and 930 may have the convolutional neural network structure, but the present disclosure is not limited thereto.

The comparator 950 may have the deep neural network, the convolutional neural network, or an arbitrary comparison algorithm structure. When the defect inspection method of the present disclosure outputs positional information of a pixel at an anomaly portion (i.e., a portion where there is the defect in the object 10) which exists in the slave image 1030, the comparator 950 may have the deep neural network structure. When the comparison method of the present disclosure outputs whether there is the anomaly portion in the slave image 1030, the comparator 950 may be configured by a mathematical comparison algorithm.

The comparator 950 may be connected to each of the sub networks 910 and 930 in series. Here, "in series" may mean that at least a part of the output of the sub network may become an input of the comparator 950 or a part of the sub network may overlap with the comparator 950. The comparator 950 may have a configuration to compare a plurality of images and features of the images, and the comparator 950 compares the features output from the respective sub networks with each other to generate comparison information. The comparator 950 may have a type of function to compare the mathematical distance between both features, and may be a component that is configured by the deep neural network to determine the similarity between both features. When the comparator 950 is configured by the deep neural network, the comparator 950 may calculate a feature related to the similarity of the image from data received from the first sub network 910 and the second sub network 930. The comparator 950 as an arbitrary data comparison algorithm may compare the features extracted from the sub networks with each other, and the present disclosure is not limited to the comparison algorithm. The comparator 950 may have the deep neural network structure and include a deconvolutional neural network structure in the deep neural network structure.

Figure 11:
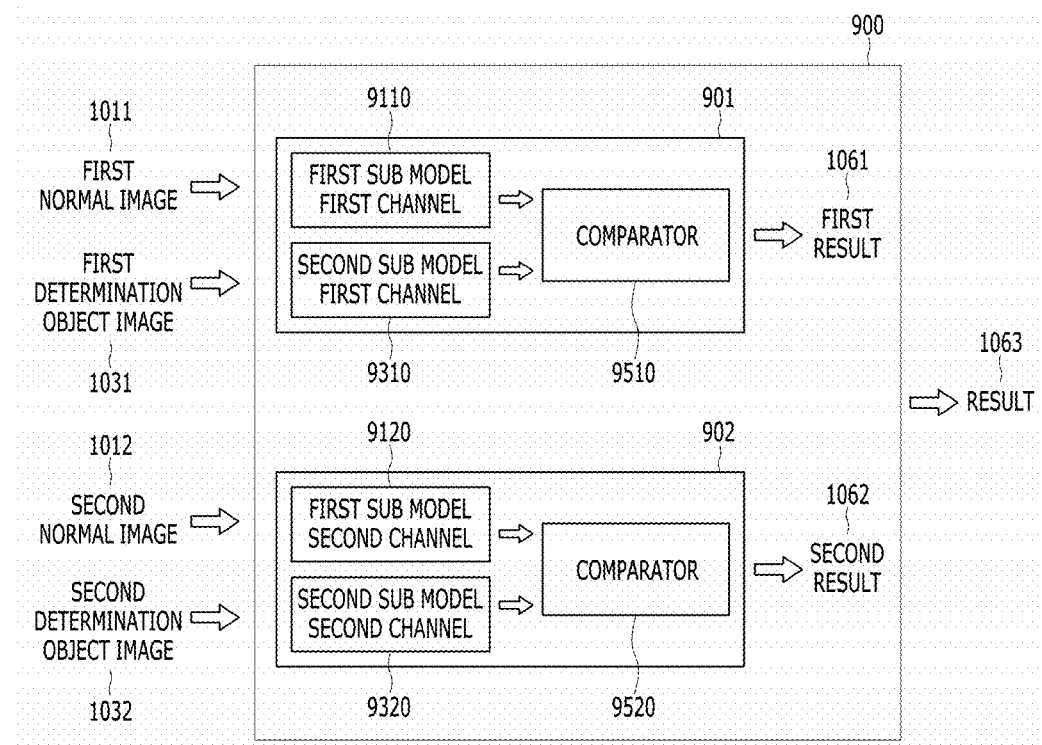
FIG. 11 is an exemplary diagram illustrating a configuration of a defect inspection model for implementing the defect inspection method according to an embodiment of the present disclosure.

Based on a comparison result of the comparator 950, the neural network 900 may output anomaly related data. The anomaly related data may include whether the image includes the anomaly data or positional information of a pixel where the anomaly exists when the image includes the anomaly data. The anomaly related data may include whether the object 10 included in the image includes the defect or positional information of a pixel where the defect exists when the object 10 includes the defect. A labeling image 1250 of FIG. 11 is an image displayed by visualizing the positional information of the pixel where the anomaly exists. The positional information of the pixel where the anomaly exists in the image is displayed in a shape overlapping with the portion where the anomaly exists in the image to be visualized. In another embodiment, the positional information of the pixel where the anomaly exists may include information which may specify a contour of a data area in which the anomaly exists. The present disclosure includes an arbitrary method for displaying the portion where the anomaly exists in the image.

FIG. 11 is an exemplary diagram illustrating a configuration of a defect inspection model for implementing the defect inspection method according to an embodiment of the present disclosure.

FIG. 11 is an exemplary diagram more specifically illustrating the exemplary diagram of FIG. 10.

The control unit 800 may determine whether there is the defect in the object 10 by using the defect inspection model 900. According to an embodiment of the present disclosure, the control unit 800 may determine whether there is the defect in the object 10 based on the image of the object 10 photographed by the first camera unit 300.

According to an embodiment of the present disclosure, the control unit 800 may determine whether there is the defect in the object 10 based on two or more images photographed under different illumination conditions, respectively. The defect inspection device 1 may input a first normal image 1011, a first determination object image 1031, a second normal image 1012, and a second determination object image 1032 into the defect inspection model 900, and output a result based on a result of calculating a similarity between both images calculated in a first channel included in the defect inspection model 900 and a similarity between both images calculated in a second channel.

The first normal image 1011 may be an image acquired based on irradiating first type of light to an object having no defect by the first sub illumination unit 210. The first determination object image 1031 may be an image acquired based on irradiating the first type of light to the object 10 by the first sub illumination unit 210. The second normal image 1012 may be an image acquired based on irradiating second type of light to the object having no defect by the second sub illumination unit 220. The second determination object image 1032 may be an image acquired based on irradiating the second type of light to the object 10 by the second sub illumination unit 220. The first normal image 1011, the first determination object image 1031, the second normal image 1012, and the second determination object image 1032 may be images acquired by photographing exteriors of objects in the same arrangement state.

The number of types of light which the illumination unit 200 irradiates to the object 10 may mach the number of determination object images and may also match the number of channels of the defect inspection model 900. For example, when the illumination unit 200 irradiates light to the objects 10 in the same arrangement state with three different types of sub illumination units to acquire an image for each of the objects 10, the defect inspection device 1 calculate respective images by the defect inspection model 900 including three channels. The detailed description of the defect inspection model 900 described above is just an example and the present disclosure is not limited thereto.

A first channel 901 of the defect inspection model 900 extracts the features from the first normal image 1011 and the first determination object image 1031, respectively, and compares the respective features to determine a first similarity. When the first similarity is equal to or less than a threshold, the first determination object image 1031 may be determined as the image including the anomaly data. The first channel 901 may output a first result 1061 based on the first similarity. A second channel 902 of the defect inspection model 900 extracts the features from the second normal image 1012 and the second determination object image 1032, respectively, and compares the respective features to determine a second similarity. The second channel 902 may output a second result 1062 based on the second similarity. When the second similarity is equal to or less than a threshold, the second determination object image 1032 may be determined as the image including the anomaly data. The defect inspection model 900 may output a result 1063 for whether there is the defect in the object 10 based on the first result 1061 and the second result 1062. When at least one of the first determination object image 1031 and the second determination object image 1032 is the image including the anomaly data, the defect inspection model 900 may output the result 1063 that there is the defect in the object 10.

Sub models 9110 and 9310 and 9120 and 9320 may constitute at least a part of the Siamese network. The sub models 9110 and 9310 of the first channel share at least a part of a weight with each other to allow a comparator 9510 to extract the features with a common weight for the first normal image 1011 and the first determination object image 1031 and compare the extracted features. The sub models 9120 and 9320 of the second channel share at least a part of a weight with each other to allow a comparator 9520 to extract the features with a common weight for the second normal image 1012 and the second determination object image 1032 and compare the extracted features. According to an embodiment of the present disclosure, since illumination conditions of images input into the first channel 901 and the second channel 902, respectively are different, each of the sub models 9110 and 9310 of the first channel and the sub models 9120 and 9320 of the second channel may not share the weight. According to another embodiment of the present disclosure, since the illumination conditions of images input into the first channel 901 and the second channel 902, respectively are different, but since the arrangement states of the objects 10 included in the images are the same, each of the sub models 9110 and 9310 of the first channel and the sub models 9120 and 9320 of the second channel may share at least a partial weight.

According to an embodiment of the present disclosure, the control unit 800 may determine whether there is the defect in the object based on two or more images acquired by photographing an object 10 in a first arrangement state under different illumination conditions and two or more images acquired by photographing an object 10 in a second arrangement state under different illumination conditions. For example, the control unit 800 may determine whether there is the defect in the object 10 based on two or more images for a first lateral surface acquired by photographing the object 10 in the first arrangement state and a second lateral surface acquired by photographing the object 10 in the second arrangement state under different illumination conditions. The detailed description of the arrangement state described above is just an example and the present disclosure is not limited thereto.

The control unit 800 may calculate two or more images acquired by photographing the object 10 in the first arrangement state under different illumination conditions by using the first defect inspection model 900 and calculate two or more images acquired by photographing the object 10 in the second arrangement state under different illumination conditions by using the second defect inspection model 900. Weights of neural networks included in the first defect inspection model 900 and the second defect inspection model 900 may be different. It may be determined whether there is the anomaly in the image acquired by photographing the object 10 in the first arrangement state by using the first defect inspection model 900 and it may be determined whether there is the anomaly in the image acquired by photographing the object 10 in the second arrangement state by using the second defect inspection model 900. When there is the anomaly in at least one of the image acquired by photographing the object 10 in the first arrangement state and the image acquired by photographing the object 10 in the second arrangement state, it may be determined that there is the defect in the object 10.

Figure 12:
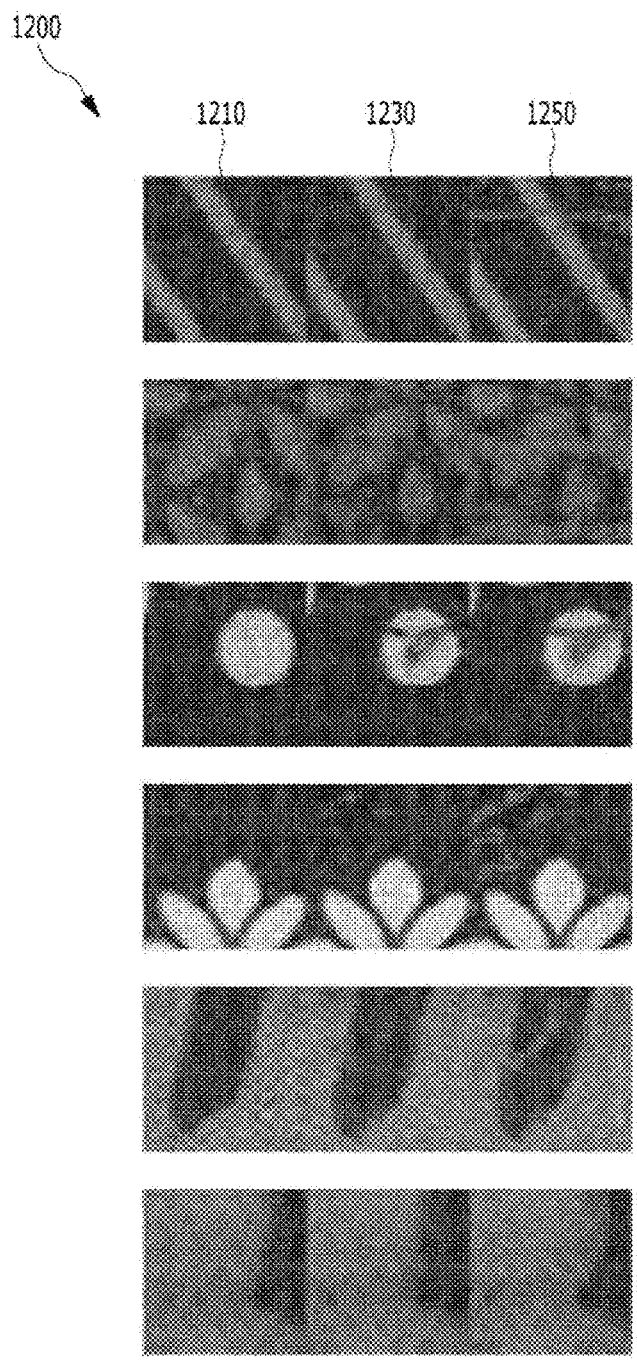
FIG. 12 illustrates an example of learning data of the defect inspection model for implementing the defect inspection method according to an embodiment of the present disclosure.

FIG. 12 illustrates an example of learning data of the defect inspection model for implementing the defect inspection method according to an embodiment of the present disclosure.

Training data 1200 for the neural network for implementing the defect inspection method according to an embodiment of the present disclosure may include a normal image 1210, an object image 1230, and a labeling image 1250. The normal image 1210 as an image which becomes a basis for determining the anomaly of the input data may be an image including only normal-state image data not including the anomaly data. The normal image 1210 may correspond to the master image 1010 of the neural network after training. That is, for example, the normal image 1210 may be an image without anomaly, which has only the anomaly pattern of the normal product. The object image 1230 as an image which becomes an anomaly determination object may be an image including the anomaly data. The object image 1230 may correspond to the slave image 1030 of the neural network after training. The labeling image 1250 is an image acquired by labeling a pixel having the anomaly in the object image 1230. The image illustrated in FIG. 12 is a product image related to a fiber processing field, but the present disclosure is not limited thereto.

Figure 13:
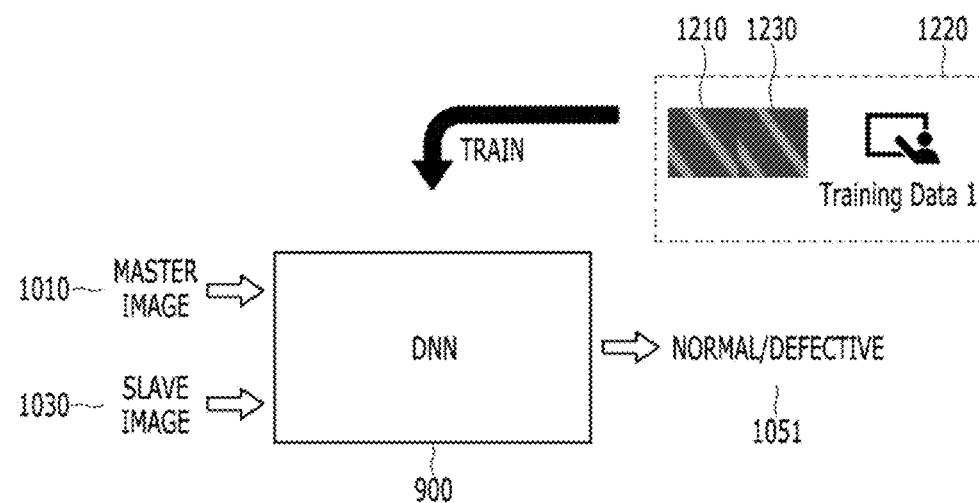
FIG. 13 is a conceptual diagram illustrating a learning scheme of the defect inspection model for implementing the defect inspection method according to an embodiment of the present disclosure.
Figure 14:
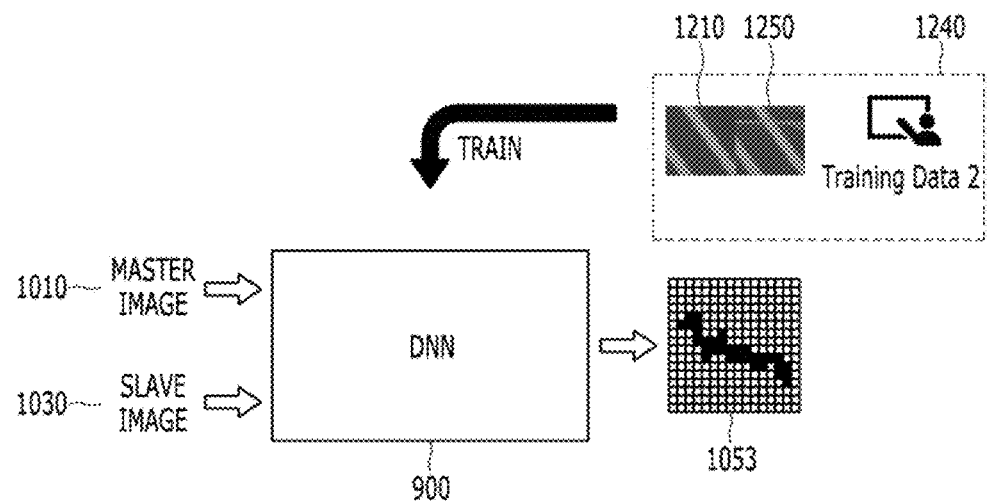
FIG. 14 is a conceptual diagram illustrating a learning scheme of the defect inspection model for implementing the defect inspection method according to another embodiment of the present disclosure.
Figure 15:
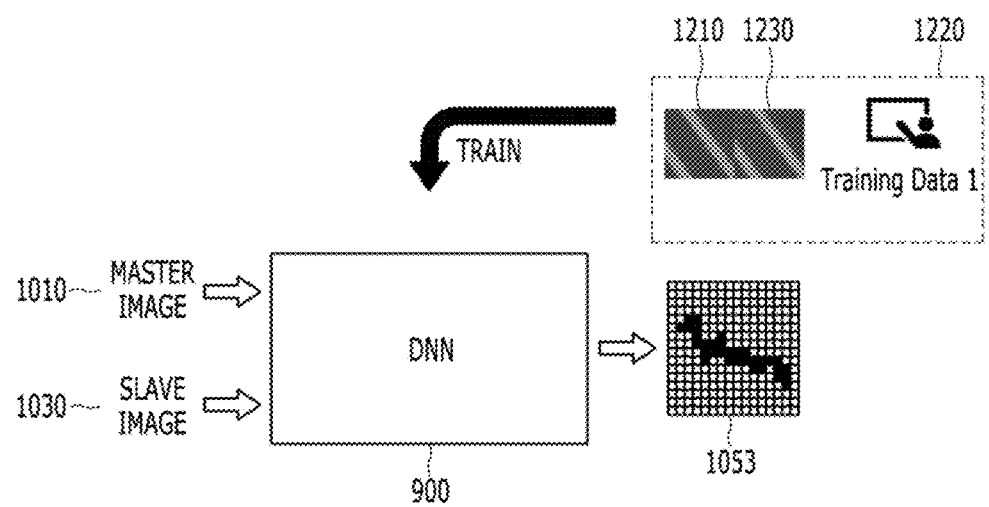
FIG. 15 is a conceptual diagram illustrating a learning scheme of the defect inspection model for implementing the defect inspection method according to yet another embodiment of the present disclosure.

FIGS. 13 to 15 are conceptual diagrams illustrating a learning scheme of the defect inspection model for implementing the defect inspection method according to an embodiment of the present disclosure.

As illustrated in FIG. 13, in an embodiment of the present disclosure, the neural network 900 trains the normal image 1210 and the object image 1230 with training data 1220 (i.e., data in which whether there is the anomaly is labeled) to be trained to determine whether input data includes the anomaly data. Here, the object image 1230 may be an image in which whether there is the anomaly is labeled. That is, in the learning scheme of FIG. 13, the normal image 1210 and the object image 1230 may be input into the neural network 900 and the neural network 900 may output an output 1051 regarding whether there is the anomaly data in the object image 1230. The control unit 800 acquires an error by comparing the output of the neural network and information regarding whether there is the anomaly data labeled to the object image 1230 and reverses the error to train the neural network 900 to classify whether there is the anomaly data from the slave image 1030. That is, the control unit 800 may train the neural network 900 so as to output the output 1051 regarding whether there is the anomaly data by using the training data 1230 in which whether there is the anomaly data is labeled.

As illustrated in FIG. 14, in another embodiment of the present disclosure, the neural network 900 may be trained to output data 1053 related to positional information of the pixel where there is the anomaly from input data by learning the normal image 1210 and the labeling image 1250 with the training data 1240 (i.e., an abnormal image in which the normal data and the pixel where there is the anomaly are labeled). Here, the labeling image 1250 may be data in which the positional information of the pixel where there is the anomaly is labeled to the image as described above. That is, in the learning scheme of FIG. 14, the normal image 1210 and the labeling image 1250 may be input into the neural network 900 and the neural network 900 may output data related to the positional information of the pixel where there is the anomaly from the labeling image 1250. The control unit 800 acquires an error by comparing the output of the neural network and data related to the positional information of the pixel where there is the anomaly labeled to the labeling image 1250 and reverses the error to train the neural network 900 to output the data related to the positional information of the pixel where there is the anomaly from the slave image 1030. That is, the control unit 800 may train the neural network 900 so as to output the output 1053 regarding the positional information of the pixel where there is the anomaly from the image data by using the training data 1240 in which the positional information of the pixel where there is the anomaly is labeled in the image data.

As illustrated in FIG. 15, in yet another embodiment of the present disclosure, the neural network 900 may be trained to output data 1053 related to the positional information of the pixel where there is the anomaly from input data by learning the normal image 1210 and the object image 1230 with the training data 1220. That is, in the learning scheme of FIG. 15, the normal image 1210 and the object image 1230 may be input into the neural network 900 and the neural network 900 may output the data related to the positional information of the pixel where there is the anomaly from the object image 1230. The control unit 800 acquires an error by comparing the output of the neural network and a target (e.g., whether there is the anomaly labeled to the object image 1230) and reverses the error to train the neural network 900 to output the data related to the positional information of the pixel where there is the anomaly from the slave image 1030. That is, the control unit 800 may train the neural network 900 so as to output the output 1053 regarding the positional information of the pixel where there is the anomaly from the image data by using the training data 1220 in which whether there is the anomaly data is labeled.

Figure 16:
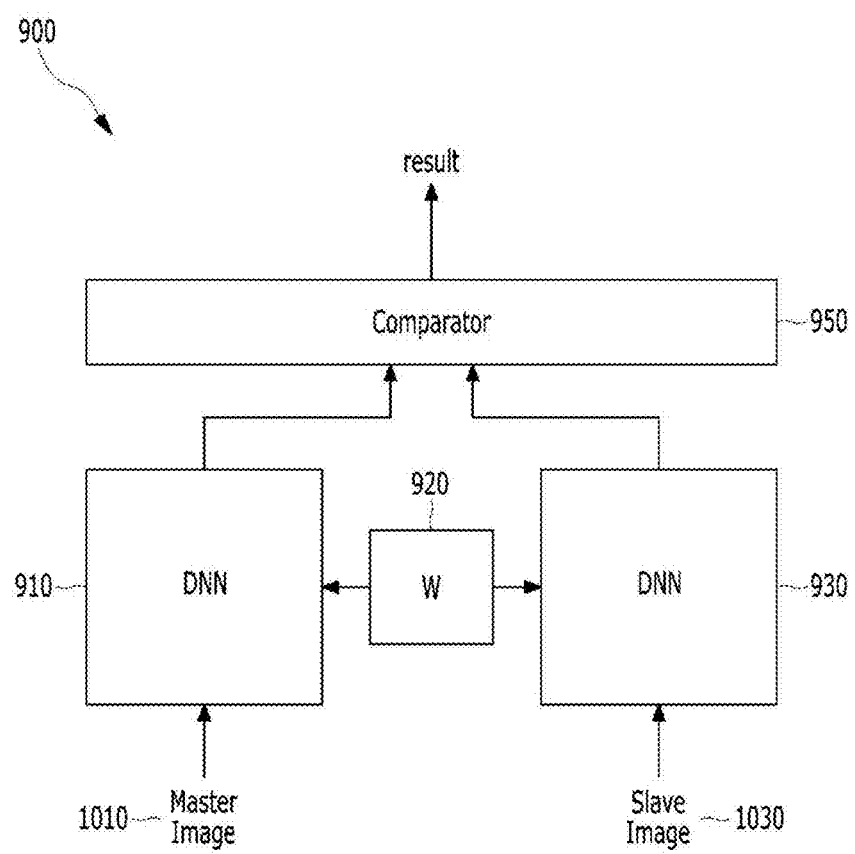
FIG. 16 is a diagram illustrating a configuration of a defect inspection model for implementing the defect inspection method according to an embodiment of the present disclosure.

FIG. 16 is a diagram illustrating a configuration of a defect inspection model for implementing the defect inspection method according to an embodiment of the present disclosure.

FIG. 16 is a diagram illustrating a Siamese network for implementing the defect inspection method according to the present disclosure. The Siamese network 900 may constitute the neural network 900 of FIG. 9. At least one of the sub networks 9110, 9120, 9310, and 9320 may include the convolutional neural network structure. The sub networks 910 and 930 may share one or more weights by the weight sharing module 920. The weight sharing module 920 may be a structure to connect the sub networks 910 and 930 so that both sub networks 910 and 930 share one or more weights. The comparator 950 may include the convolutional network structure. The sub networks 910 and 930 may share at least a part of the weight with each other. Accordingly, the sub networks 910 and 930 extract the features for the master image 1010 and the slave image 1030 with a common weight to allow the comparator 950 to compare the extracted features.

The comparator 950 may constitute at least a part of a U network structure with at least one of respective sub networks. The U network 1300 will be described with reference to FIG. 17. All or some of the sub networks 910 and 930 and all or some of the comparators 950 may constitute the U network. In addition, a combination of the sub networks 910 and 930 and the comparator 950 may be a part of the U network 1300.

Figure 17:
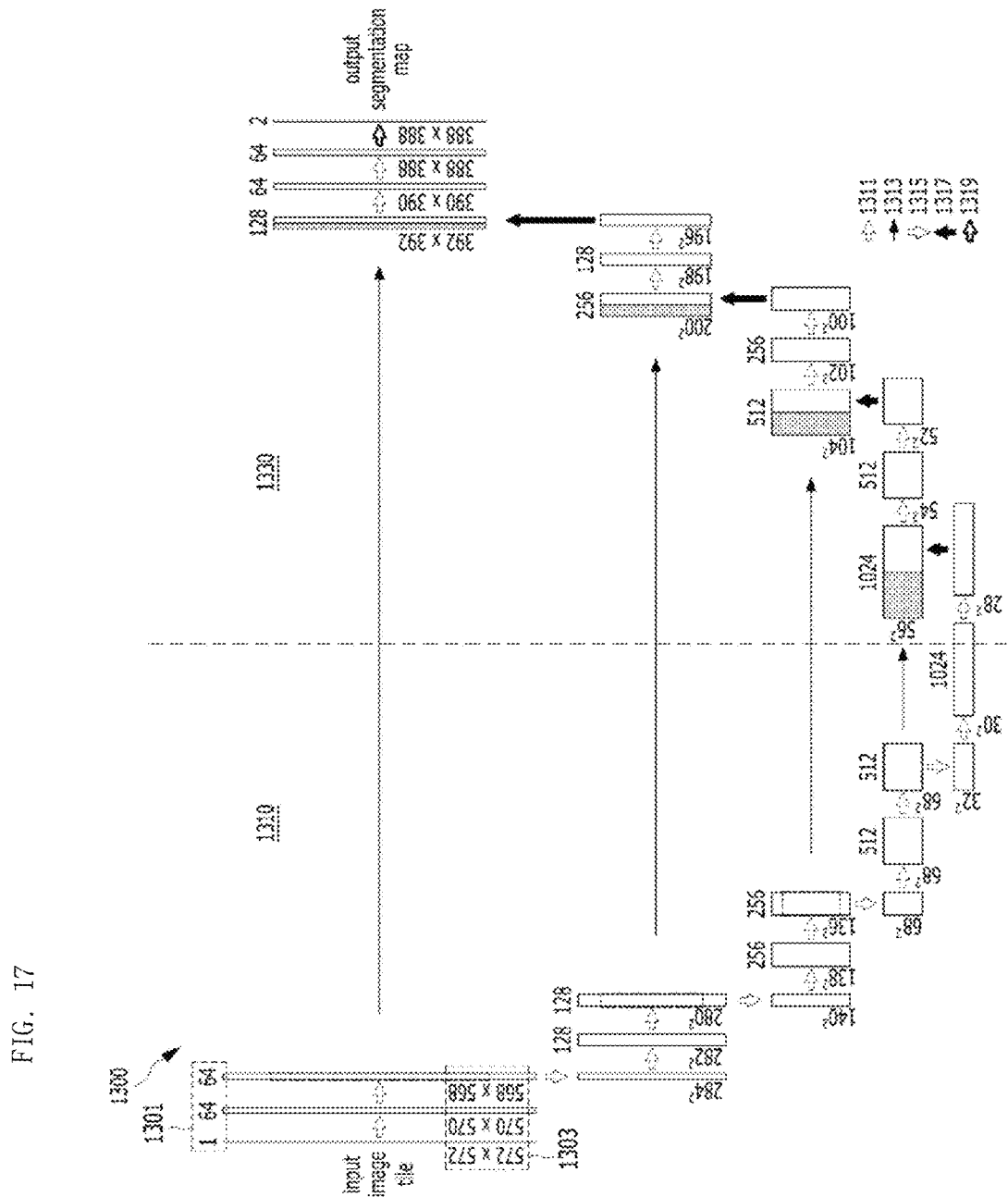
FIG. 17 is an exemplary diagram of a U network for implementing a defect inspection method according to an embodiment of the present disclosure.

The U network 1300 may be the deep neural network structure capable of performing the image segmentation. A left part of the U network illustrated in FIG. 17 may have a deep neural network structure capable of reducing a dimension of input data and a right part may have a deep neural network structure capable of increasing the dimension of the input data. More specifically, a dimension reduction network 1310 of the U network 1300 may have the convolutional neural network structure and a dimension increase network 1330 may have the deconvolutional neural network structure. A portion displayed in a rectangular shape, which is illustrated in FIG. 17 may be each layer of the U network. A number of portion 1301 of each layer illustrated in FIG. 17 may be a number of exemplary channels of each layer. A number of portion 1303 of each layer illustrated in FIG. 17 may mean a number of exemplary pixels of an image processed by each layer and when following an arrow direction of a calculation of the U network illustrated in FIG. 17, it can be seen that the dimension of the image is reduced, and then increased in that the number of exemplary pixels of the image is reduced, and then increased. Arrow 511 illustrated in FIG. 17 may mean a convolutional operation to apply a convolutional filter to the image. For example, arrow 511 may represent a convolutional operation to apply a 3*3 convolutional filter to the image, but the present disclosure is not limited thereto. Arrow 1313 illustrated in FIG. 17 may mean an operation to transmit information required for increasing a dimension of an image of which dimension is reduced to the dimension increase network 1330 corresponding to the dimension reduction network 1310. Arrow 1315 illustrated in FIG. 17 may mean a pooling operation for reducing the pixel of the image. For example, arrow 1315 may be max pooling that extracts a maximum value, but the present disclosure is not limited thereto. Arrow 1317 illustrated in FIG. 17 may mean a convolutional operation to increase the dimension of the image. For example, arrow 1317 may represent a convolutional operation to apply a 2*2 convolutional filter, but the present disclosure is not limited thereto. Arrow 1319 illustrated in FIG. 17 may mean a convolutional operation for transferring an output to a fully connected layer. For example, arrow 1319 may represent a convolutional operation using a 1*1 convolutional filter. A slashed rectangle included in the dimension increase network 1330 illustrated in FIG. 17 may mean that information for increasing the dimension of the image is transferred from a layer corresponding to the dimension reduction network 1310.

The U network 1300 may have a structure (arrow 1313 illustrated in FIG. 17) to transfer the information (e.g., positional information of the pixel, a high-level feature, etc.) for the increasing the dimension in the process of reducing the dimension of the image to the process of increasing the image dimension for the image segmentation. That is, each layer of the dimension reduction network 1310 of the U network may transfer the positional information of the feature to the layer corresponding to the dimension increase network 1330. As a result, positional information of a pixel which may be lost in the process of reducing the dimension of the image, and then increasing the dimension may be reconstructed. Accordingly, since the positional information of the pixel may be reconstructed in the process of increasing the image dimension, the U network may use the positional information of the pixel for required image segmentation. Specifically, as in the example illustrated in FIG. 17, a first layer (a layer closest to an input) in the dimension reduction network 1310 of the U network 1300 may transfer information to a last layer (a layer closest to an output) of the dimension increase network 1330. The transferred information may include required for increasing the dimension of the image of which dimension is reduced in the dimension increase network 1330. The transferred information may be, for example, a feature, positional information of the feature, positional information of a pixel from which each feature is extracted, pixel positional information of an original image, etc., but the present disclosure is not limited thereto. In addition, a second layer (a second layer in the input) in the dimension reduction network of the U network may transfer information to a second layer (a second layer in the output) at the end of the dimension increase network 1330. In this process, each sub network (the dimension increase network 1330 or the dimension reduction network 1310) of the U network may transfer information to a corresponding layer determined based on the position of the layer.

Figure 18:
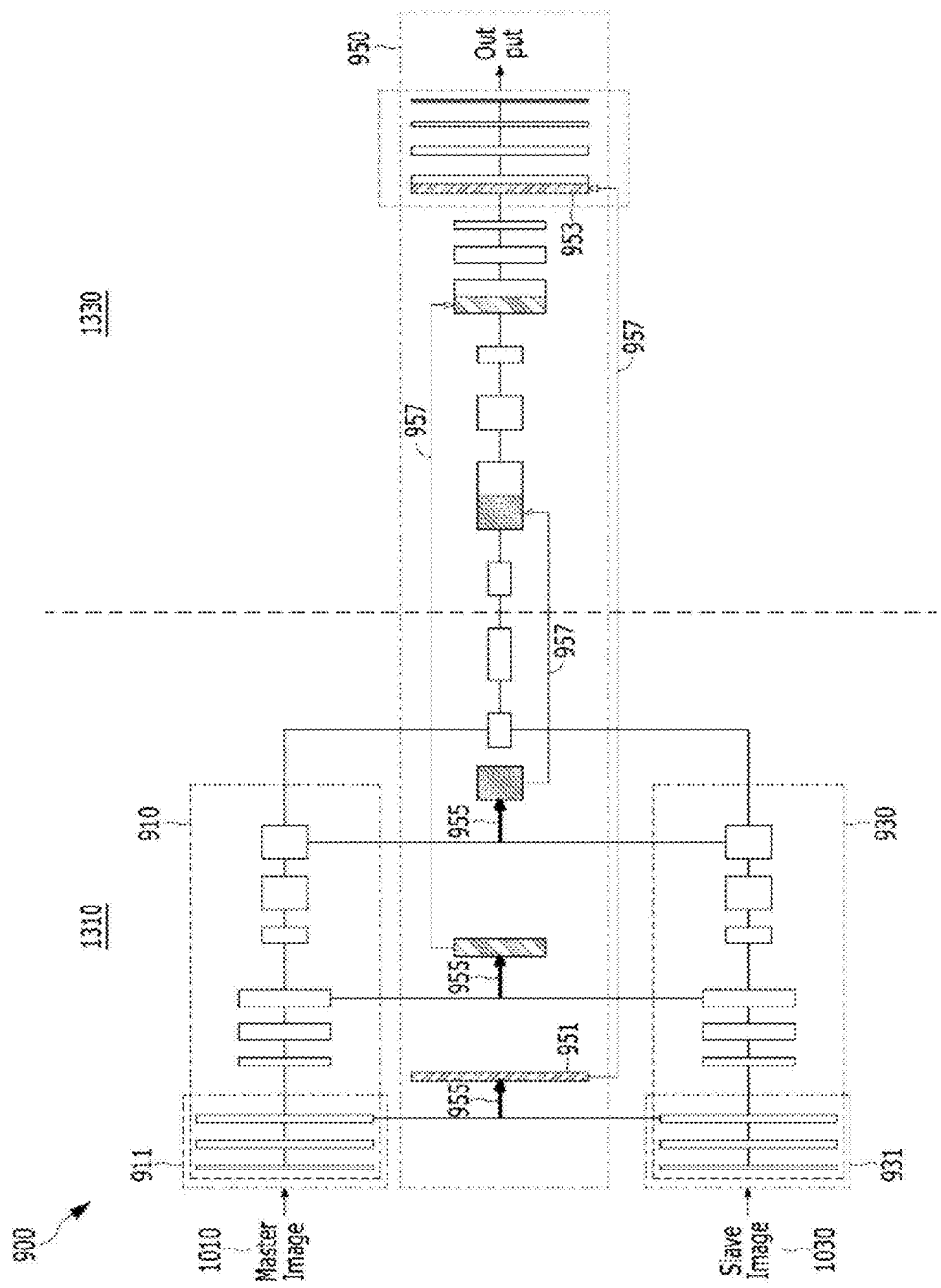
FIG. 18 is an exemplary diagram of a Siamese network for implementing a defect inspection method according to another embodiment of the present disclosure.

The comparator 950 includes the dimension increase network to constitute at least a part of the U network structure with at least one of the sub networks 910 and 930. FIG. 18 as an exemplary diagram of a Siamese network for implementing the defect inspection method of the present disclosure is a diagram illustrating that the sub networks 910 and 930 constitute the U network structure with the comparator 950. In the example of FIG. 18, a rectangle of one group may represent layer 1 of the neural network. The neural network configured in FIG. 18 is just a simplified example, and the number of layers, a size of the image, etc., may be changed, and the present disclosure is not limited to the description of FIG. 18.

In FIG. 18, a left side of a dotted line may indicate the dimension reduction network 1310 for reducing the dimension of the input data of the U network and a right side of the dotted line may configure the dimension increase network 1330 for reconstructing the dimension of the input data.

In the example of FIG. 18, the master image 1010 may be input into the first sub network 910 and the slave image 1030 may be input into the second sub network 930. The first sub network 910 may extract the feature from the master image 1010 and the second sub network 930 may extract the feature from the slave image 1030. In this case, the first sub network 910 and the second sub network 930 may share the weight with each other. Features of respective layers of the first sub network 910 and the second sub network 930 may be compared with each other. Arrow 955 illustrated in FIG. 18 may mean an operation to derive data from the first and second sub networks. For example, arrow 955 may mean an operation to compare data calculated in the first and second sub networks. Further, for example, arrow 955 may mean a calculation of a difference between a master image feature and a slave image feature or a deep neural network comparator operation of the master image feature and the slave image feature. Each of the features extracted from the respective layers of the first and second sub networks 930 may be compared by the comparator 950. The control unit 800 compares the features extracted from the respective layers of the first and second sub networks 930 to generate layer comparison information. The layer comparison information may include information on a difference between the master image feature and the slave image feature. The control unit 800 may calculate anomaly related information based on the layer comparison information. To this end, the control unit 800 may provide the generated layer comparison information and the feature information to the layer corresponding to the comparator 950. The provided information may be the feature, the positional information of the feature, the positional information of the pixel from which each feature is extracted, the pixel positional information of the original image, the layer comparison information, etc. The corresponding layer is determined based on a position of the layer of the first sub network or the layer of the second sub network which becomes a basis to generate the layer comparison information. More specifically, a layer close to an input layer of the first and second sub networks corresponds to a layer close to the output of the comparator 950. A pattern illustrated in the rectangle illustrated in FIG. 18 may mean that both layers are layers corresponding to each other. That is, the first layers 911 and 931 of the first and second sub networks illustrated in FIG. 18 may correspond to a third layer of the comparator 950. That is, a position of a layer based on the input layer of the first and second sub networks and a position of a layer based on the output layer of the comparator 950 may correspond to each other. That is, first layer comparison information 951 illustrated in FIG. 18 may be transferred to the third layer 953 of the dimension increase network 930 of the comparator 950. Arrow 957 illustrated in FIG. 18 may mean an operation to transfer information derived from the first and second sub networks to a corresponding layer which belongs to the dimension increase network 930. Further, arrow 957 may mean transferring information for increasing the reduced dimension of the image. Arrow 957 means transferring and connection of the layer comparison information and the feature information, and this is a similar operation to arrow 1313 illustrated in relation to the U network of FIG. 17. In respect to the Siamese network of FIG. 18, the sub networks (the sub network and the comparator) of the Siamese network constitute the U network structure to reconstruct the positional information of the pixel which may be lost in the process of reducing the dimension of the image, and then increasing the dimension as the layer comparison information 951 is transferred to the dimension increase network 930. Accordingly, the defect inspection method of the present disclosure has the neural network structure illustrated in FIG. 18 to perform the image segmentation for the anomaly part.

In the present disclosure, the neural network 900 may classify whether the anomaly data is included in the slave image 1030 based on the difference between the master image 1010 and the slave image 1030. Further, in the present disclosure, the neural network 900 may display a pixel in an anomaly part which exists in the slave image 1030 based on the difference between the master image 1010 and the slave image 1030, and the layer comparison information.

By using a neural network adopting the Siamese network, the defect inspection method according to an embodiment of the present disclosure may train and classify both a case where the master image and the slave image are partially different (a case where both images are much similar, but some anomaly exists, and as a result, some details are different) and a case where the master image and the slave image are significantly different (when both images are significantly different, but there is no anomaly due to lens distortion, an illumination change, a different texture, etc., and as a result, details are similar). The defect inspection method of the present disclosure may determine whether the anomaly data exists in the slave image due to a difference in detail when the master image and the slave image belong to the same domain. Specifically, when both the master image and the slave image are images for a fabric including a floral pattern (in the case of the same pattern and the same texture), a portion where there is a difference between both images may be the anomaly data. Further, the defect inspection method of the present disclosure may determine whether the anomaly data exists in the slave image by comparing details even when the master image and the slave image belong to different domains. Specifically, when the master image is an image for a fabric including the floral pattern and the slave image is an image for a leather including a start pattern (when patterns and textures are different), a portion having a large difference generated due to different domains in both images are disregarded and the details are examined to determine whether there is the anomaly data in the slave image. Therefore, since the defect inspection method of the present disclosure may have a general recognition capability even for rotation of image data, transformation, an error due to lens distortion, domain change, etc., there is an effect of overcoming a limit of the existing neural network that the training data should be secured for each domain and training should be performed for each domain.

Mode for Disclosure

Related contents in the best mode for carrying out the present disclosure are described as above.

Industrial Applicability

The present disclosure can be used for automation equipment, a machine, and a device used in a factory.

The invention claimed is:

1. A defect inspection device comprising:
   a robot arm including a hold unit for holding an object and a driving unit for moving the object;
   a first camera unit photographing an exterior of the object;
   an illumination unit irradiating light to the exterior of the object; and
   a control unit determining whether there is a defect in the object based on an image of the object photographed by the first camera unit, wherein the control unit determines whether there is the object based on two or more images photographed under different illumination conditions, respectively, and
   wherein the control unit
   calculates a first normal image photographed under a first illumination condition and a second normal image photographed under a second illumination condition which are normal images which are a basis of anomaly determination by using both images as inputs of channels included in a first sub model included in a defect inspection model, respectively,
   calculates a first determination object image photographed under the first illumination condition and a second determination object image photographed under the second illumination condition which are anomaly determination object images by using both images as inputs of channels included in a second sub model included in the defect inspection model, respectively, and
   determines whether there is the defect in the object based on a calculation result of the first sub model and the second sub model.

2. The defect inspection device of claim 1, further comprising:
   a display unit displaying at least one image of the image of the object photographed by the first camera unit and an image in which whether there is the defect in the object is displayed.

3. The defect inspection device of claim 1, further comprising:
   a transport unit transporting the object for defect inspection; and
   a classification transport unit classifying and transporting the object based on a result of the defect inspection of the control unit for the object.

4. The defect inspection device of claim 1, wherein the driving unit includes at least one driving shaft for rotating the object.

5. The defect inspection device of claim 1, wherein the driving unit adjusts an arrangement state of the object so that the first camera unit photographs the object in a different arrangement state to acquire images photographed at different timings.

6. The defect inspection device of claim 1, further comprising:
   a second camera unit for photographing the object before being held by the hold unit,
   wherein the control unit allows the hold unit to be aligned to hold the object based on the arrangement state of the object based on the image of the object acquired by the second camera unit.

7. The defect inspection device of claim 1, wherein the illumination unit includes two or more sub illumination units irradiating light, and the illumination unit has a space formed therein,
   the first camera unit is located on one side of the space and photographs an object arranged on the other side of the space by the robot arm through the space, and
   the control unit allows the robot arm to arrange the object on the other side of the space so that the first camera unit photographs the object.

8. The defect inspection device of claim 7, wherein in the sub illumination unit, a light emitting unit configured in a corn or polypyramid shape, and irradiating light to an internal surface of a horn shape is located.

9. The defect inspection device of claim 7, wherein the two or more sub illumination units are configured in the corn or polypyramid shape, and ratios of widths of lower surfaces and widths of upper surfaces of the horn shape of respective sub illumination units are different from each other.

10. The defect inspection device of claim 1, wherein the illumination unit irradiates two or more different types of light to the exterior of the object.

11. The defect inspection device of claim 1, wherein the control unit determines whether there is the defect in the object based on two or more images acquired by photographing an object in a first arrangement state under different illumination conditions and two or more images acquired by photographing an object in a second arrangement state under different illumination conditions.

12. The defect inspection device of claim 1, wherein the control unit sets the two or more images as inputs of two or more channels included in the defect inspection model including one or more network functions, respectively to extract features of the two or more input images, respectively by using the defect inspection model, and determines whether there is anomaly for each of the two or more images based on the extracted features.

13. The defect inspection device of claim 12, wherein when it is determined that there is the anomaly in at least one image of the two or more images, the control unit determines that there is the defect in the object.

14. The defect inspection device of claim 1, wherein the defect inspection model further includes a comparator connected to at least one of the first sub model and the second sub model in series.

15. The defect inspection device of claim 1, wherein a first channel of the first sub model into which the first normal image is input shares at least one link having the same weight as a first channel of the second sub model into which the first determination object image is input, and
   a second channel of the first sub model into which the second normal image is input shares at least one link having the same weight as a second channel of the second sub model into which the second determination object image is input.

16. The defect inspection device of claim 1, wherein the control unit
   generates comparison information of at least one first layer based on at least one layer of the first channel of the first sub model and at least one layer of the first channel of the second sub model, and transfers the first layer comparison information to a corresponding layer of the first channel of the comparator to calculate anomaly information of the first determination object image, and generates comparison information of at least one second layer based on at least one layer of the second channel of the first sub model and at least one layer of the second channel of the second sub model, and transfers the second layer comparison information to a corresponding layer of the second channel of the comparator to calculate the anomaly information of the second determination object image.

\* \* \* \* \*